(12) United States Patent
Nakamura et al.

(10) Patent No.: US 7,569,351 B2
(45) Date of Patent: Aug. 4, 2009

(54) P53 DEPENDENT APOPTOSIS-ASSOCIATED GENE AND PROTEIN

(75) Inventors: Yusuke Nakamura, Kanagawa (JP); Hirofumi Arakawa, Tokyo (JP)

(73) Assignee: Oncotherapy Science, Inc., Kanagawa (JP)

( * ) Notice: Subject to any disclaimer, the term of this patent is extended or adjusted under 35 U.S.C. 154(b) by 25 days.

(21) Appl. No.: 10/343,733

(22) PCT Filed: Aug. 2, 2001

(86) PCT No.: PCT/JP01/06666

§ 371 (c)(1),
(2), (4) Date: May 19, 2003

(87) PCT Pub. No.: WO02/12496

PCT Pub. Date: Feb. 14, 2002

(65) Prior Publication Data

US 2004/0038243 A1 Feb. 26, 2004

(30) Foreign Application Priority Data

Aug. 3, 2000 (JP) ............................. 2000-240399

(51) Int. Cl.
| | |
|---|---|
| C07H 21/04 | (2006.01) |
| C12N 15/63 | (2006.01) |
| C12N 15/85 | (2006.01) |
| C12N 15/86 | (2006.01) |
| C12N 1/21 | (2006.01) |
| C12N 1/15 | (2006.01) |
| C12N 1/19 | (2006.01) |
| C12N 5/14 | (2006.01) |
| C12N 15/00 | (2006.01) |
| C07K 5/00 | (2006.01) |
| C07K 14/00 | (2006.01) |
| C12Q 1/00 | (2006.01) |
| G01N 33/53 | (2006.01) |

(52) U.S. Cl. ..................... 435/7.1; 536/23.5; 536/23.1; 435/252.3; 435/254.11; 435/254.2; 435/320.1; 435/325; 435/419; 435/69.1; 435/70.1; 435/71.1; 435/4; 530/300; 530/350; 530/395

(58) Field of Classification Search ...................... None
See application file for complete search history.

(56) References Cited

U.S. PATENT DOCUMENTS

| | | | |
|---|---|---|---|
| 5,789,201 | A | 8/1998 | Guastella |
| 6,083,735 | A | 7/2000 | Yuan et al. |
| 6,087,160 | A | 7/2000 | Yuan et al. |
| 6,214,572 | B1 | 4/2001 | Yuan et al. |
| 6,416,753 | B1 | 7/2002 | Yuan et al. |
| 6,812,339 | B1 * | 11/2004 | Venter et al. ............. 536/24.31 |
| 2002/0132767 | A1 * | 9/2002 | Rosen et al. ................... 514/12 |
| 2003/0049709 | A1 | 3/2003 | Yuan et al. |
| 2004/0033502 | A1 * | 2/2004 | Williams et al. ............... 435/6 |

FOREIGN PATENT DOCUMENTS

| | | |
|---|---|---|
| JP | 2000-83672 | 3/2000 |
| JP | 2000-210089 | 8/2000 |
| WO | WO 96/12017 | 4/1996 |
| WO | WO 98/42835 | 10/1998 |
| WO | WO 99/52925 | 10/1998 |
| WO | WO 98/57664 | 12/1998 |

OTHER PUBLICATIONS

Gomez-Manzano, C. et al "Adenovirus-mediated transfer of the p53 gene produces rapid and generalized death of human glioma cells via apoptosis" Cancer Research (1996) 56:694-699.*
Witkowski et al., Biochemistry, vol. 38, pp. 11643-11650, 1999.*
Dang et al., Clin. Cancer Res., vol. 5, pp. 471-474, 1999.*
King et al., Annu. Rev. Physiol., vol. 60, pp. 601-617, 1998.*
Brown, T., "Current Protocols in Molecular Biology"(Unit 2.9A) pp. 1-2 and (Unit 2.10), pp. 1-16, 1993.*
Fox, J., Nat. Biotechnol., vol. 21, p. 217, 2003.*
Attardi, L.D., et al., "PERP, an apoptosis-associated target of p53, is a novel member of the PMP-22/gas3 family," *Genes & Develop.* 14:704-718, Cold Spring Harbor Laboratory Press (Mar. 2000).
Kroemer, G., "The proto-oncogene Bcl-2 and its role in regulating apoptosis," *Nat. Med.* 3:614-620, Nature Publishing Group (1997).
Lacanà, E., et al., "Dissociation of Apoptosis and Activation of IL-1β-Converting Enzyme/Ced-3 Proteases by *ALG-2* and the Truncated Alzheimer's Gene *ALG-3*," *J. Immunol.* 158:5129-5135, American Association of Immunologists (1997).
Miyashita, T. and Reed, J.C., "Tumor Suppressor p53 Is a Direct Transcriptional Activator of the Human *bax* Gene," Cell 80:293-299, Cell Press (1995).
Müller, M., et al., "p53 Activates the CD95 (APO-1/Fas) Gene in Response to DNA Damage by Anticancer Drugs," *J. Exp. Med.* 188:2033-2045, The Rockefeller University Press (1998).
Nakano, K. and Vousden, K.H., "*PUMA*, a Novel Proapoptotic Gene, Is Induced by p53," Mol. Cell 7:683-694, Cell Press (Mar. 2001).
Oda, E., et al., "Noxa, a BH3-Only Member of the Bcl-2 Family and Candidate Mediator of p53-Induced Apoptosis," *Science* 288:1053-1058, American Association for the Advancement of Science (May 2000).

(Continued)

*Primary Examiner*—Rebecca E Prouty
*Assistant Examiner*—Jae W Lee
(74) *Attorney, Agent, or Firm*—Sterne, Kessler, Goldstein & Fox P.L.L.C.

(57) ABSTRACT

A novel apoptosis-associated gene p53AIPI is isolated by screening for a gene the expression of which is induced by p53. Since the protein encoded by this gene has an activity of inducing apoptosis, this gene is useful in developing effective therapeutic agents for cancer mediated by apoptosis. A method of screening for a compound controlling the induction of apoptosis which is expected as being useful in developing an apoptosis controlling agent.

8 Claims, 25 Drawing Sheets

OTHER PUBLICATIONS

Oda, K., et al., "p53AIP1, a Potential Mediator of p53-Dependent Apoptosis, and Its Regulation by Ser-46-Phosphorylated p53," *Cell* 102:849-862, Cell Press (Sep. 2000).

Polyak, K., et al., "A model for p53-induced apoptosis," *Nature* 389:300-305, Nature Publishing Group (1997).

Resnick-Silverman, L., et al., "Identification of a novel class of genomic DNA-binding sites suggests a mechanism for selectivity in target gene activation by the tumor suppressor protein p53," *Genes & Develop.* 12:2102-2107, Cold Spring Harbor Laboratory Press (1998).

Ryan, K.M. and Vousden, K.H., "Charactization of Structural p53 Mutants Which Show Selective Defects in Apoptosis but Not Cell Cycle Arrest," *Mol. Cell. Biol.* 18:3692-3698, American Society for Microbiology (1998).

Saller, E., et al., "Increased apoptosis induction by 121F mutant p53," *EMBO J.* 18:4424-4437, Oxford University Press (Aug. 16, 1999).

Tanaka, H., et al., "A ribonucleotide reductase gene involved in a p53-dependent cell-cycle checkpoint for DNA damage," *Nature* 404:42-49, Nature Publishing Group (Mar. 2000).

Tokino, T., et al., "p53 tagged sites from human genomic DNA," *Human Mol. Genet.* 3:1537-1542, Oxford University Press (1994).

Vito, P., et al., "Interfering with Apoptosis: $Ca^{2+}$-Binding Protein ALG-2 and Alzheimer's Disease Gene ALG-3," *Science* 271:521-525, American Association for the Advancement of Science (1996).

Yu, J., et al., "PUMA Induces the Rapid Apoptosis of Colorectal Cancer Cells," *Mol. Cell.* 7:673-682, Cell Press (Mar. 2001).

International Search Report for International Patent Application No. PCT/JP01/06666, mailed Nov. 6, 2001.

Dialog File 351, Accession No. 10725049, Derwent English language abstract for WO 96/12017 (Document AL1).

Dialog File 351, Accession No. 12115094, Derwent English language abstract for WO 98/42835 (Document AM1).

Patent Abstracts of Japan, English language abstract for JP2000-083672 (Document AP1).

Patent Abstracts of Japan, English language abstract for JP2000-210089 (Document AL2).

* cited by examiner

FIG. 3

```
α  MGSSSEASFRSAQASCSGARRQGLGRGDQNLSVMPPNGRAQTHTPGWVS DPLVLGAQVHGGC
β  MGSSSEASFRSAQASCSGARRQGLGRGDQNLSVMPPNGRAQTHTPGWVS DPLVLGAQVHGGC
γ  MGSSSEASFRSAQASCSGARRQGLGRGDQNLSVMPPNGRAQTHTPGWVS PCSENRDGLLPAT

α  RGIEALSVSSGSWSSATVWILT GLGLGLSRPFLPGATVLRDRPLGSAFELSYDQKKAPLRLQ
β  RGIEALSVSSGSWSSATVWILT VQ
γ  APGRLCSHRGADIPSFQTHQDPVTASGSSELHADCPQFRALDRAGN
```

FIG. 6
| FITC (Anti-HA) | Rhodamine (Mitochondria) | FITC + Rhodamine |
|---|---|---|
|  | 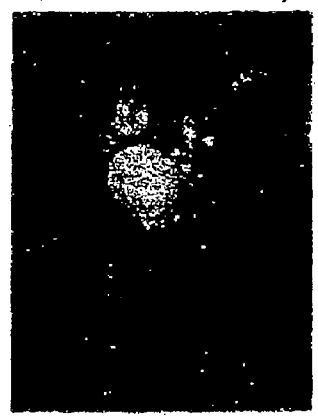 |  |

FIG. 9
| | Rhodamine | FITC (TUNEL) | Rhodamine + FITC | TUNEL-positive (%) |
|---|---|---|---|---|
| p53AIP1 |  |  |  | 55.3 ± 8.6 |
| p53WT |  |  |  | 60.0 ± 8.9 |
| p53mt |  |  |  | 17.7 ± 2.5 |

P53 DEPENDENT APOPTOSIS-ASSOCIATED GENE AND PROTEIN

TECHNICAL FIELD

The present invention relates to a novel p53-dependent apoptosis-associated protein and gene encoding the protein as well as the preparation and use thereof, and, furthermore, a method of screening for an apoptosis controlling compound.

BACKGROUND ART

The cancer suppressor protein p53 is known to be stabilized and activated by diverse cellular stresses such as heat shock, hypoxia, osmotic shock, and DNA damage, leading to the inhibition of cell growth and apoptosis (Ko and Prives, Genes Dev. 10: 1054-1072, 1996; Levine, Cell 88: 323-331, 1997; Oren, Cancer Biol. 5: 221-227, 1994). However, almost nothing is known as to how p53 selects the pathway of cell growth inhibition or apoptosis.

It has been also known that appptosis and cell cycle arrest are the major tumor suppressing function of p53 (Levine, Cell 88: 323-331, 1997). Therefore, the elucidation of mechanism of p53-induced apoptosis may contribute to the development of anticancer agents having a novel mechanism of action in the cancer treatment. Induction of apoptosis due to the expression of exogenous p53 has been reported in some, though not all, cancer cells with the p53 mutation (Gomez-Manzano etal., Cancer Res. 56: 694-699; Kock et al., Int. J. Cancer 67: 808-815, 1996). Therefore, if the apoptosis-associated target gene of p53 is identified and allowed to express in cancer cells, or a protein encoded by the gene is introduced into the cancer cell, thereby inducing apoptosis, effective cancer treatment would be possible. Besides cancer, examples of apoptosis-associated disorders include arteriosclerosis, Alzheimer's disease, amyotrophic lateral sclerosis, graft-versus-host disease, autoimmune lymphocytosis syndrome, and viral infection. The identification of apoptosis-associated p53 target gene would greatly contribute to the elucidation of causes for these disorders or development of their effective therapy.

Furthermore, a mitochondrial protein bcl-2 has been known to inhibit the apoptosis process, promoting cell survival (Vaux, D. L. et al., Nature, 335: 440-442, 1988; Tsujimoto, Y. Oncogene, 4: 1331-1336, 1989; Sentman, C. L. et al., Cell, 67: 879-888, 1991; Strasser, A. Cell, 67: 889-899, 1991). Bcl-2 gene was first isolated as an oncogene activated by the chromosome translocation in a human follicular lymphoma (Tsujimoto, Y. et al., Science (Washington D.C.), 226: 1097-1099, 1984; Bakhshi, A. Cell, 41: 899-906, 1985; Cleary, M. L. et al., Proc. Natl. Acad. Sci. USA, 82:7439-7443, 1985). In *Caenorhabditis elegans*, ced-3 and ced-4 are essential for apoptosis during development, while ced-9 inhibits their actions (Ellis, H. M. and Horvitz, H. R. Cell, 44: 817-829, 1986; Hengartner, M. O. and Horvitz, H. R. Curr. Opin. Genet. Dev., 4: 581-586, 1994). Since bcl-2 is functionally as well as structurally a human homolog of ced-9 (Hengartner, M. O. and Horvitz, H. R. Cell, 76: 665-676, 1994), this mechanism of apoptosis seems to be extremely well conserved from nematodes to mammals. Although the major action mechanism of bcl-2 is uncertain, the bcl-2 gene product is thought to directly or indirectly interfere with the release of cytochrome c from mitochondria (Yang, J. et al., Science (Washington D.C.) 275: 1129-1132, 1997; Kluck, R. M. et al., Science (Washington D.C.), 275: 1132-1136, 1997; Shimizu, S., et al., Nature, 399: 483-487, 1999). Bcl-2 contains four functional domains called BH1, BH2, BH3, and BH4 (Reed, J. C. Oncogene, 17: 3225-3236, 1998). More than seventeen distinct members of the bcl-2 family proteins have been reported as an anti-apoptosis factor or apoptosis inducer, all of which contain at least one of these four different domains.

The majority of mechanisms of the p53-dependent apoptosis, which is thought to be the most important characteristic of cancer suppression by p53, have not been elucidated. Several target genes have been isolated as those encoding candidate proteins associated with the p53-dependent apoptosis, including Bax (Miyashita, T. and Reed, J. C. Cell, 80: 293-299, 1995), PIG3 (Polyak, K., et al., Nature, 389: 300-305, 1997; Venot, C. et al., EMBO J., 17: 4668-4679, 1998), *Killer/DR5* (Wu, G. S., et al., Nat. Genet., 17: 141-143, 1997), Fas (Owen-Schaub, L. B., et al., Mol. Cell Biol., 15: 3032-3040, 1995; Muller, M., et al., J. Exp. Med., 188: 2033-2045, 1998), Noxa (Oda, E., et al., Science (Washington D.C.), 288: 1053-1058, 2000), PERP (Attardi, L. D., et al., Genes Dev., 14: 704-718, 2000), and PUMA (Nakano, K. and Vousden, K. H., Mol. Cell, 7: 683-694, 2001; Yu, J., et al., Mol. Cell, 7: 673-682, 2001). Bax, Noxa, and PUMA are mitochondrial proteins, containing the BH-3 domain, and belong to the bcl-2 family. PIG3 is a homolog of the plant NADPH oxidoreductase TED2 involved in the apoptosis process necessary for the formation of plant meristem. Killer/DR5 and Fas are receptors to transmit the external cell death signal. PERP is a cellular plasma membrane protein whose overproduction induces apoptosis. Indeed these known target genes encode candidate proteins involved in the p53-dependent apoptosis but they are not sufficient for explaining the mechanism of p53-induced apoptosis.

Knowledge obtained by elucidating the cancer suppression mechanism of p53, and in particular the mechanism of p53-mediated apoptosis, are expected to lead to the development of novel drugs having the different mechanism of action from the conventional one, especially apoptosis-mediated cancer therapeutic agents.

DISCLOSURE OF THE INVENTION

As described above, many points of the mechanism of p53-mediated apoptosis remain to be clarified. Therefore, a primary objective of the present invention is to elucidate the mechanism of p53-induced apoptosis. Another objective is to provide a novel apoptosis-associated protein induced by p53-mediated transcription, and gene encoding the protein. Furthermore, based on the knowledge obtained by elucidated apoptosis mechanism, a novel method of screening for compounds that control apoptosis and apoptosis-controlling agents are to be provided.

To reach at the above-described objectives, the present inventors conducted exhaustive studies as described below. First, the present inventors attempted to isolate a gene whose expression is induced by p53, that is, a target gene for which p53 functions as a transcription factor. The gene isolation was performed using a yeast enhancer trap system capable of directly cloning the p53-binding sequence in the human genomic DNA (Tokino et al., Hum. Mol. Genet. 3: 1537-1542, 1994), thereby isolating a number of human genomic sequences whose transcriptions are thought to be activated by p53. Then, one of these sequences (clone TP53-41), a 190 bp DNA fragment, was sequenced to reveal that the clone actually contained a sequence assumed to be the p53-binding sequence (BDS). Next, a cosmid clone carrying the sequence was isolated from the human cosmid library, and the nucleotide sequence of the entire genomic sequence contained in the cosmid clone was determined by the shotgun sequencing to predict exons using a computer program (GRAIL2) Using a probe prepared based on the predicted exon sequence, a cDNA library of glioblstoma U373MG cells (obtained from ATCC) infected with Adenovirus (Ad-p53) that is deficient in the. replication potency and expresses the wild-type p53, was screened. Twenty positive clones were obtained, and these cDNA clones were sequenced to identify three main transcripts named α, β, and γ comprising 806, 777, and 2659 nucleotides, respectively, and containing ORFs encoding 124, 86, and 108 amino acids, respectively. It was found that these three transcripts were produced from a single gene by alternative splicing. The gene was found not to be homologous to any known genes, proved to be a novel gene, and designated p53AIP1 (p53-regulated Apoptosis Inducing Protein 1). The p53AIP1 gene contains five exons over a stretch of 8.2 kb. Northern blotting analysis revealed its expression only in the thymus among normal human tissues.

Next, the present inventors examined whether p53 actually binds to the above-described BDS to induce the expression of p53AIP1 gene or not. As a result, p53 binds to BDS and activates the transcription of the gene, indicating that the p53AIP1 gene is the direct target gene of p53.

Apoptosis is known to be induced by DNA damage. To investigate the association of p53AIP1 gene with apoptosis, the present inventors examined whether the γ irradiation to cells containing the wild-type p53 or exposure of the cells to Adriamycin induces the endogenous p53AIP1 expression. As a result, the expression of p53AIP1 was proved to be induced in response to DNA damage.

The present inventors also examined whether p53AIP1α, β and γ proteins themselves have the function as a cell proliferation inhibitor or not. The result revealed that p53AIP1α and β have the activity to inhibit the cell proliferation, and that the intracellular expression of p53AIP1α protein induced apoptosis.

Then, the present inventors examined whether the inhibition of endogenous p53AIP1 expression would suppress the p53-dependent apoptosis or not. To inhibit the expression of p53AIP1, sense and antisense oligonucleotides corresponding to a portion of p53AIP1 cDNA sequence were prepared and introduced into the cell nucleus. As a result, the induction of p53AIP1 expression as well as that of the p53-dependent apoptosis was remarkably inhibited. These results proved that p53AIP1 is an important factor associated with the p53-dependent apoptosis.

To determine whether p53AIP1 is a common mediator in various apoptosis pathways or not, the present inventors examined the p53AIP1 function with respect to three distinct apoptosis stimulators, staurosporine (STS), UV irradiation, and TNFα that causes apoptosis independently from the mitochondrial pathway. The results showed that, during the apoptosis induction by STS, or UV irradiation, the dose-dependent p53AIP1 expression remarkably increased, but not in response to TNFα, revealing the association. of p53AIP1 with the apoptosis pathway mediated by mitochondria. Furthermore, it was revealed that the ectopic expression of p53AIP1 in human cells induced the down regulation of mitochondrial membrane potential and release of cytochrome c from mitochondria.

The immunoprecipitation and immunostaining. experiments revealed that p53AIP1 interacts with bcl-2 protein in mitochondria, and that this interaction influences on the p53AIP1-associated apoptosis mediated by the regulation of mitochondrial membrane potential.

As described above, the transcription target gene of p53, p53AIP1, itself has the activity to suppress the cell proliferation via apoptosis and functions to induce apoptosis, and is thus useful in the development of effective cancer therapeutic agents mediated by apoptosis in particular. Furthermore, p53AIP1 is also useful as the target molecule in the development of therapeutic agents for apoptosis-associated diseases.

The present invention has been accomplished based on the above-described findings, and provides a novel gene p53AIP1 associated with p53-dependent apoptosis, a protein encoded by the gene, a novel method of screening for compounds that control apoptosis, and an apoptosis-controlling agent.

More specifically, the present invention relates to:

(1) a DNA of the following (a) or (b):
(a) a DNA encoding a protein comprising the amino acid sequence of any one of SEQ ID NOs: 2, 4, and 6, or
(b) a DNA comprising the coding region of nucleotide sequence of any one of SEQ ID NOs: 1, 3, and 5;

(2) a DNA of the following (a) or (b) encoding a protein having the activity to induce apoptosis:
(a) a DNA encoding a protein comprising the amino acid sequence of any one of SEQ ID NOs: 2, 4, and 6 wherein one or more amino acids are substituted, deleted, inserted, and/or added, or
(b) a DNA hybridizing to the DNA comprising the nucleotide sequence of any one of SEQ ID NOs: 1, 3, and 5 under stringent conditions;

(3) a DNA-encoding a partial peptide of proteins comprising the amino acid sequence of any one of SEQ ID NOs: 2, 4, and 6;

(4) a protein or peptide encoded by the DNA of any one of (1) to (3);

(5) a vector comprising the DNA of any one of (1) to (3)

(6) a host cell carrying the DNA of any one of (1) to (3), or the vector of (5);

(7) a method for producing the protein or peptide of (4), the method comprising the steps of culturing the host cells of (6) and recovering the expressed protein from said host cells or the culture supernatant thereof;

(8) an antibody binding to the protein or peptide of (4);

(9) a polynucleotide containing at least 15 nucleotides complementary to the DNA comprising the nucleotide sequence of any one of SEQ ID NOs: 1, 3, and 5, or to the complementary strand thereof;

(10) an antisense polynucleotide to the DNA comprising the nucleotide sequence of any one of SEQ ID NOs: 1, 3, and 5;

(11) a method of screening for a candidate compound for an apoptosis controlling agent, the method comprising the steps of:
(a) contacting a test sample with the protein or peptide of (4),
(b) detecting the binding activity of the test sample to said protein or peptide, and
(c) selecting a compound having the activity to bind to said protein or peptide;

(12) a method of screening for a candidate compound for a apoptosis controlling agent, the method comprising the steps of:
(a), contacting a test sample with cells containing a vector having the structure in which a p53-binding sequence and a reporter gene are operably linked,
(b) measuring the expression level of said reporter gene, and,
(c) selecting a compound capable of decreasing or increasing the expression level of said reporter gene measured in the step (b) compared to that measured in the absence of the test sample;

(13) a method of screening for a candidate compound for a apoptosis controlling agent, the method comprising the steps of:

(a) contacting a test sample with the protein or peptide of (4), and bcl-2 protein,
(b) measuring the binding activity of said protein or peptide to bcl-2 protein, and
(c) selecting a compound capable of decreasing or increasing the binding activity measured in the step (b) compared to that measured in the absence of the test sample;
(14) an apoptosis controlling agent containing the compound selected. by the method of any one of (11) to (13) as an effective ingredient;
(15) an apoptosis inhibitor containing the antisense polynucleotide of (10) as an effective ingredient; and
(16) an apoptosis accelerating agent containing the DNA of any one of (1) to (3) or a vector comprising the DNA as an effective ingredient.

The present invention relates to novel p53-dependent apoptosis-associated proteins "p53AIP1α", "p53AIP1β", and "p53AIP1γ" whose expressions are induced by p53. RNA transcripts encoding the respective proteins are produced from the novel "p53AIP1" gene of the present invention by alternative splicing. The cDNA nucleotide sequences of "p53AIP1α", "p53AIP1β", and "p53AIP1γ" of the present invention thus isolated are shown in SEQ ID NOs: 1, 3, and 5, respectively. Amino acid sequences of proteins "p53AIP1α", "p53AIP1β", and "p53AIP1γ" encoded by the cDNAs are shown in SEQ ID NOs: 2, 4, and 6, respectively. Furthermore, the nucleotide sequence (9305 bp) of the genomic DNA of "p53AIP1" gene of this invention is shown in SEQ ID NO: 7. Exon regions encoding constitutive "p53AIP1α", "p53AIP1β", and "p53AIP1γ" proteins of this invention are as follows:

p53AIPα, β, γ exon 1, 910-1043 bp;
p53AIPα, β exon 2, 5941-6157 bp;
p53AIPα, β exon 3, 7186-7297 bp;
p53AIPα exon 4, 8123-8465 bp;
p53AIPβ exon 4, 8791-9104 bp; and
p53AIPγ exon 2, 5941-6665 bp.

Unless otherwise stated, "p53AIP1α", "p53AIP1β", and "p53AIP1γ" proteins of this invention are hereinafter collectively described as "p53AIP1" proteins.

The protein encoded by "p53AIP1" gene has the function associated with p53-dependent apoptosis and is thus useful as the target molecule in the development of preventive and therapeutic agent for apoptosis-associated disorders. Furthermore, since "p53AIP1α" and "p53AIP1β" proteins have the cell proliferation suppressing activity, and their intracellular expressions induce apoptosis, they themselves are expected to be used as drugs for cancer treatment.

The present invention includes proteins structurally analogous to "p53AIP1" proteins as long as they have the activity to induce apoptosis by their intracellular expressions. Such structurally analogous proteins include mutant of "p53AIP1" proteins and "p53AIP1" proteins derived from other organisms. Whether cells undergo apoptosis or not can be determined by usual methods performed by those skilled in the art such as TUNEL method or LM-PCR method using various commercially available kits. More specifically, as shown in Example 6, TUNEL method can be carried out using Apotag Direct (oncor) according to the attached manual. Apoptosis can be also examined by LM-PCR using an ApoAlert LM-PCR ladder assay kit (Clontech) according to the attached manual.

Those skilled in the art can prepare such proteins by, for example, known methods for mutagenesis. Examples of methods well-known to those skilled in the art for modifying amino acids in proteins are site-directed mutagenesis methods such as the method with deletion-mutant preparation (Kowalski. D. et al., 1976, J. Biochem., 15, 4457; McCutchan, T. F. et al., 1984, Science, 225, 626-628), Kunkel method (Kunkel, T. A., 1985, Proc. Natl. Acad. Sci. USA 82: 488-492; Kunkel, T. A. et al., 1987, Methods Enzymol. 154: 367-382), Gapped-duplex method (Kramer, W. and Fritz, H.-J., 1987, Methods Enzymol. 154: 350-367; Zoller, M. J. and Smith, M., 1983, Methods Enzymol. 100: 468-500; Hirose, S., 1991, Muramatsu, M. and Okayama, H. ed., JIKKEN IGAKU, Supplement, Genetic Engineering Handbook, Yodosha, pp. 246-252), PCR method (Muramatsu, M. ed. Labomanual IDENSI KOGAKU, 3$^{rd}$ ed., Maruzen, Co., 1996, pp. 227-230), and cassette mutation method (Kishimoto, T., 1991, Muramatsu, M. and Okayama, H., ed., JIKKEN IGAKU, Supplement, Genetic Engineering Handbook, Yodosha, pp. 253-260). For example, a Transformer™ Site-Directed Mutagenesis Kit (CLONTECH #K1600-1).

When artificial modification in the proteins is performed, usually 30 amino acids or less, preferably 10 amino acids or less, and more preferably 5 amino acids or less are modified. Amino acid mutation in proteins. can also occur in nature. The present invention also includes proteins having amino acid sequences altered from those of the natural "p53AIP1" proteins (SEQ ID NO: 2, 4, or 6) due to the artificial or natural substitution, deletion, addition, and/or insertion of amino acids as long as they have the activity to induce apoptosis when intracellularly expressed.

Preferably, an amino acid can be substituted with the one having similar property to that of the amino acid to be substituted. For example, since Ala, Val, Leu, Ile, Pro, Met, Phe, and Trp are all classified into the non-polar amino acids, they are thought to have similar properties each other. Non-charged amino acids are exemplified by Gly, Ser, Thr, Cys, Tyr, Asn, and Gln, while acidic amino acids include Asp and Glu, and basic amino acids include Lys, Arg, and His.

In addition, "p53AIP1" proteins with additional amino acid includes a fusion protein of "p53AIP1" proteins with other peptides.

Proteins structurally analogous to "p53AIP1" proteins having the activity to induce apoptosis when intracellularly expressed can be prepared using well-known hybridization technique (SAIBOU KOGAKU, Supplement 8, New Cell Technology Experimental Protocol, 1991, Shujunsha, pp. 188-193 and 79-87; Sambrook, J. et al., Molecular Cloning, Cold Spring Harbor Laboratory Press (1989), 8.46-8.52) and polymerase chain reaction technique (SAIBOU KOGAKU, Supplement 8, New Cell Technology Experimental Protocol, 1991, Shujunsha, pp. 171-186; Sambrook, J. et al., Molecular Cloning, Cold Spring Harbor Laboratory Press (1989), 14.1-14.35). That is, those skilled in the art routinely obtain proteins structurally analogous to "p53AIP1" proteins from a variety of organisms by isolating DNAs highly homologous to "p53AIP1" cDNA using "p53AIP1" cDNA sequences (SEQ ID NOs: 1, 3, or 5) or portions thereof as a probe, and oligonucleotides. specifically hybridizing to the "p53AIP1" cDNA sequences (SEQ ID NOs: 1, 3, or 5) as a primer, and preparing proteins based on DNAs thus isolated.

The present invention includes proteins encoded by DNAs hybridizing to "p53AIP1" cDNA as long as they have the activity to induce apoptosis when intracellularly expressed. Examples of organisms useful in isolating such proteins include monkey, rat, mouse, rabbit, goat, cattle, and pig, but not limited to them. For isolating DNAs encoding such proteins, thymocytes of these organisms may be suitable as a source.

DNAs encoding "p53AIP1" proteins derived from organisms other than humans are usually highly homologous to the nucleotide sequence of "p53AIP1" cDNA (SEQ ID NO: 1, 3, or 5). High homology refers to the sequence identity of at least 60% or more, preferably 80% or more, further preferably 90% or more at the amino acid level. Sequence identity can be determined by a homology search program of DNA Data Bank of Japan (National Institute of Genetics: Yata 1111, Mishima, Shizuoka 411, Japan).

Those skilled in the art can appropriately select hybridization conditions for isolating DNAs encoding proteins functionally equivalent to the "p53AIP1" proteins. For example, the pre-hybridization is carried out in a hybridization solution containing 25% formamide (50% formamide under the stringent conditions), 4×SSC, 50 mM Hepes (pH 7.0), 10×Denhardt's solution, and 20 μg/ml denatured salmon sperm DNA at 42° C. overnight, and then the hybridization is carried out by followed by the incubation at 42° C. overnight after the addition of a labeled probe. Then washing is carried out at room temperature in 2×SSC containing 0.1% SDS (at 50° C. in 0.5×SSC containing 0.1% SDS under the stringent conditions). Those skilled in the art can appropriately change a plurality of the factors thought to affect the stringency of hybridization such as temperature. and concentrations of formamide and salts so as to achieve the same stringency as above (SAIBOU KOGAKU, Supplement 8, New Cell Technology Experimental Protocol, 1991, Shujunsha, pp. 79-87). Further guidelines concerning hybridization are readily available in the art, for example, from Sambrook, et al. (Molecular Cloning, A Laboratory Manual, Cold Spring Harbor Press, N.Y., 1989) and Ausubal, et al. (Current Protocols in Molecular Biology, unit 2.10 (John Wiley & Sons, N.Y. )).

The protein of this invention can be prepared not only as a natural protein but also as a recombinant protein prepared by the gene recombination technique. The natural protein can be prepared, for example, by applying extracts of. tissues (e.g. thymocytes), in which the "p53AIP1" protein is thought to be expressed, to affinity chromatography using the antibody against the "p53AIP1" protein described below. On the other hand, the recombinant protein may be prepared, as described below, by culturing cells transformed with DNA encoding the "p53AIP1" protein to express the protein therein and then recovering it.

The present invention also includes partial peptides of the protein of this invention, such as partial peptides containing the region comprising 10 amino acids on the N-terminus and/or the region containing 10 amino acids on the C-terminus of the protein of this invention. The N-terminal peptide is -essential for localization in mitochondria and the C-terminal peptide is useful as an immunogen for preparing antibody.

The partial polypeptides comprising amino acid sequences characteristic of the protein of the present invention contain at least seven, preferably at least eight, and more preferably at least nine amino acids. The partial peptides of this invention can be prepared, for example, by the genetic engineering technique, peptide synthesis methods well-known in the art, or cleavage of the protein of this invention with a suitable peptidase.

The partial peptides of the present invention can be used as an immunogen in preparing antibodies which recognize the protein of this invention as described below.

The present invention also relates to DNA encoding the protein of this invention. The type of DNAs encoding the proteins of this invention is not limited as long as they are capable of encoding the proteins, and includes cDNA, genomic DNA, synthetic DNA, and DNAs comprising nucleotide sequences resulted from the degeneracy of genetic codes.

The cDNA encoding the protein of this invention can be screened, for example, by labeling cDNA of SEQ ID NO: 1, 3, or 5 or fragments thereof, RNA complementary thereto, or synthetic oligonucleotide containing partial sequence of the cDNA with a label such as $^{32}P$, and hybridizing the labeled nucleotide to a cDNA library derived from tissues (e.g. bone marrow, spleen) expressing the protein of this invention. Alternatively, cDNA encoding the protein of this invention can be cloned by synthesizing oligonucleotides corresponding to these cDNA nucleotide sequences, and then amplifying them by polymerase chain reaction (PCR) with cDNA derived from the appropriate tissue (e.g. thymocytes) as a template. Synthetic DNAs can be prepared, for example, by chemically synthesizing oligonucleotides comprising partial sequences of cDNAs of SEQ ID NO: 1, 3, or 5, allowing each oligonucleotide to anneal, thereby forming the double-strand, and then ligating the products using DNA ligase.

These DNAs are useful in producing recombinant proteins. They can be used to prepare the protein of this invention as a recombinant protein by inserting DNA (e.g. DNA of SEQ ID NO: 1, 3, or 5) which encodes the protein of this invention into an appropriate expression vector, transducing suitable cells by the vector, culturing the resulting transformant, and purifying the protein expressed by the transformant. Since the protein of this invention is a secretory protein, it can be prepared by allowing it to express in mammalian cells and secrete extracellulary.

Specific examples of vectors for expressing the protein of this invention in *Escherichia coli* include pKK223-3, pKK233-2, and pJLA502. The protein of this invention can be also expressed as a fusion protein with other proteins. Vectors for fusion protein expression are exemplified by pRIT2T, pGEX-2T, and pGEX-3X. The fusion protein can be easily recovered using an affinity column. The use of a vector having the thrombin- or factor Xa-cleavage site at the border region of the fusion partners enables the excision of only the target protein. Examples of vectors for. secretion of proteins into periplasm or outside of cells include pKT280 and pRIT5 (Okada, M. and Miyazaki, K., ed. Formidable Biotechnical Series. Protein Experimental Note, I, Extraction and Separation/Purification, Yodosha, 1996, pp. 139-149).

It is also possible to express the protein of this invention in insect and mammalian cells using baculoviruses. An example of baculoviral vector used in mammalian cells is pAcCAG-MCS1 (Muramatsu, M., ed. Laboratory Manual for Gene Technology, $3^{rd}$ ed., Maruzen, 1996, pp. 242-246).

Recombinant proteins expressed in host cells can be purified by the method well-known in the art. When the protein of this invention is expressed in the form of a fusion protein linked to the histidine residue tag, glutathione-S-transferase (GST), or such at the N-terminus, it can be purified through a nickel column, glutathione Sepharose column, and such.

The DNA encoding the protein of the present invention may also be applied to the gene therapy of disorders caused by its mutation. Examples of vectors used for the gene therapy are viral. vectors such as retroviral vector, adenoviral vector, adeno-associated viral vector, vaccinia viral vector, lentiviral vector, herpesviral vector, alphaviral vector, EB viral vector, papilomaviral vector, and foamyviral vector, and non-viral vectors such as cationic liposome, ligand DNA complex, and gene gun (Y. Niitsu and M. Takahashi, Molecular Medicine, Vol. 35, No. 11, 1385-1395, 1998). Gene transduction may be carried out in vivo and ex vivo, and also co-transduction with a gene of other cytokines may be carried out.

The present invention also relates to, polynucleotides complementary to DNAs comprising nucleotide sequence of SEQ ID NO: 1, 3, or 5, or to complementary strands thereof, comprising at least 15 nucleotides (for example, 20 or more, 30 or more, and 50 or more nucleotides). Preferably, the polynucleotides specifically hybridize to DNA comprising the nucleotide sequence of SEQ ID NO: 1, 3, or 5. Herein, the phrase "specifically hybridize" means that no significant cross-hybridization to DNAs encoding other proteins occurs under the above-described usual hybridization conditions, and preferably under stringent hybridization conditions. These polynucleotides include probes and primers as well as nucleotides or derivatives thereof (e.g. ribozymes) capable of specifically hybridizing to the DNAs-encoding the protein of this invention or complementary DNAs thereto.

Oligonucleotides containing the cDNAs encoding the proteins of this invention or partial sequences thereof can be used in cloning genes and the cDNAs encoding the proteins of this invention or amplifying them by PCR. Furthermore, they can be used in detecting polymorphism or abnormality (for gene diagnosis) in the genes or cDNAs by the methods such as restriction fragment length polymorphism (RELP) analysis and single-stranded DNA conformation polymorphism (SSCP) analysis.

The present invention also relates to antisense polynucleotides of the DNAs encoding the proteins of this invention. The antisense polynucleotides of this invention would suppress the expression of the proteins of the present invention, and useful in developing reagents for elucidating mechanisms of disorders associated with p53-dependent apoptosis and drugs for the treatment of the disorders. The antisense polynucleotides of this invention comprise those hybridizing to some sites in the nucleotide sequence, for example, SEQ ID NO: 1, 3, or 5. Although the antisense polynucleotides need not be completely complementary to the nucleotide sequence of SEQ ID NO: 1, 3, or 5, or partial sequence thereof as long as they are capable of effectively inhibiting the expression of the proteins of this invention, they are preferably antisense polynucleotides to at least continuous 15 or more nucleotides in the nucleotide sequence of SEQ ID NO: 1, 3, or 5, and more preferably the continuous 15 or more nucleotides comprise the transcription initiation codon.

The antisense polynucleotides of the present invention would be applied to, for example, gene therapy. Preferable target disorders for the gene therapy may be, for example, cancers associated with p53 abnormalities and various apoptosis-related disorders. When these molecules are used in gene therapy, they may be administered ex vivo or in vivo to patients using, for example, viral vectors such as retroviral vector, adenoviral vector, and adeno-associated vector, and non-viral vector such as liposome.

The present invention also relates to antibodies binding to the protein of this invention. The antibodies of this invention includes both polyclonal and monoclonal antibodies. The polyclonal antibodies can be prepared, for example, according to the method as described in SAIBOU KOGAKU, Supplement 8, New Cell Technology Experimental Protocol, 1993, Shujunsha, pp. 202-217), Institute of Medical Science, University of Tokyo, Department of Oncology (ed.). For example, animals such as rabbits, guinea pigs, mice, and chicken are immunized with the purified protein of this invention, partial peptide thereof, or peptide synthesized based on the amino acid sequence of the protein of this invention by injecting it into the ear vein, peritoneal cavity, subcutaneous tissue, muscle, inguinal region, behind the digit nail, or such. Antigenic protein may be administered together with Freund's complete adjuvant and Freund's incomplete adjuvant. Usually the administration is performed every several weeks, and the antibody titer may be raised by booster. Periodical blood sampling is conducted to confirm the antibody titer elevation by ELISA and such, and, after the final immunization, the blood is collected from the immunized animal to obtain the antiserum. IgG fraction can be purified from the antiserum by salting-out, ion exchange chromatography, HPLC, etc. Antibodies can be further purified by affinity chromatography using the immobilized antigen.

The monoclonal antibodies can be prepared according to the method, for example, as described by Koike, T. and Taniguchi, M. 1991, Muramatsu, M. & Okamoto, H. ed., JIKKEN IGAKU, Supplement, Gene Technology Handbook, Yodosha, pp. 70-74). More specifically, the protein of this invention or partial peptide thereof is similarly used to immunize animals as described above, and, after the final immunization, spleen or lymph node is collected from the immunized animal. Antibody-producing cells contained in the spleen or lymph node are fused with myeloma cells using polyethylene glycol or such to prepare hybridoma. Target hybridomas are screened and cultured, and then the monoclonal antibody can be prepared from the culture supernatant thereof. The monoclonal antibody can be purified as IgG fraction by, for example, salting-out, ion exchange chromatography, HPLC, etc. In addition, antibody can be further purified by affinity chromatography using the immobilized antigen.

The antibody obtained by immunizing animals with the protein of the present invention or partial peptide thereof may be used not only in the affinity purification of the protein of this invention but also, for example, in the test and diagnosis of abnormality in expression and structure of the protein of this invention and detection of expression level of the protein of this invention. More specifically, the presence of abnormalities in expression and structure of the protein of this invention can be tested and diagnosed through the detection of the protein in protein samples extracted, for example, from tissues, blood, or cells by analyzing method such as Western blotting, immunoprecipitation, and ELISA.

Human monoclonal antibodies can be prepared, for example, as described by Isogai, H., 1988, JIKKEN IGAKU, Vol. 6, No. 10, 55-60, or by using the molecular biological technique as described by T. Tsunenari et al., 1996, Anticancer Res., 16, 2537-2544.. Human antibodies may also be prepared by immunizing the protein of this invention to mouse in which immune system has been replaced with that of human.

Furthermore, the present invention relates to a method of screening for candidate compounds for an apoptosis controlling agent as described below. The screening method of this invention comprises the steps of: (a) contacting a test sample with the protein of this invention or partial peptide thereof; (b) detecting the binding activity of the test sample to the protein or partial peptide thereof; and (c) selecting a compound having activity to bind to the protein or partial peptide thereof.

The apoptosis controlling agent of this invention includes apoptosis inhibitor and accelerator.

Proteins binding to the protein of the present invention may be screened, for example, by loading the culture supernatant or extracts of cells that presumably express a protein capable of binding to the protein of this invention onto an affinity column to which the protein of this invention has been immobilized, and then purifying a protein specifically binding to the affinity column.

Furthermore, the screening may be carried out according to the "West western blotting method" which comprises the steps of: (i) preparing a cDNA library, using a phage vector, from tissues or cells (e.g. thymocytes) that presumably express a protein binding to the protein of this invention, (ii) expressing the cDNA library on agarose, (iii) transferring the protein onto a membrane, and (iv) reacting it with the labeled protein of this invention to detect plaques expressing the binding protein, "two-hybrid system" which comprises the steps of: (i) expressing GAL4 DNA binding region and GAL4 transcription activation region as a fusion protein with the protein of this invention and a test protein, respectively, and (ii) detecting the binding of the protein of this invention to the test protein through the expression of a reporter gene linked downstream of the promoter having the binding sequence of the GAL4 DNA binding protein, etc.

Furthermore, methods well-known to those skilled in the art, including a method of screening for the binding molecules by reacting the immobilized protein of the present invention with synthetic compounds, natural product bank, or a random phage peptide display library, and a method of isolating a compound binding to the protein of this invention by high throuput screening for combinatorial chemistry can also be used.

Examples of test samples used in the screening include, not limited thereto, cell extracts, expression products of gene library, synthetic low molecular weight compounds, synthetic peptides, and natural compounds. Test samples used in the screening may be appropriately labeled as necessary. Labeling is exemplified by radiolabeling and fluorescence labeling, but not limited thereto.

Examples of test samples include cell extracts, expression products of a gene library, synthetic low molecular weight compounds, proteins, natural or synthetic peptides, natural compounds, and sera, but not limited thereto. Compounds isolated by the above-described screening using the binding activity to the protein of this invention as an indicator may also be used as a test sample. The protein of this invention used in the screening may be either a purified protein or culture supernatant of the transformant secreting the protein of this invention.

Since the protein of this invention "p53AIP1" has the function to induce apoptosis, compounds binding to the protein would control the apoptosis induction by the protein. Therefore, compounds obtained, by this screening method may be used as a preventive or therapeutic agent for disorders caused by, for example, abnormality in apoptosis mediated by the protein "p53AIP1", and further to a therapeutic agent for cancer by inducing apoptosis in cancer cells.

The present invention also relates to a method of screening for candidate compounds for an apoptosis controlling agent as described below. The screening method of this invention comprises the steps of: (a) contacting a test sample with cells containing a vector having the structure in which the p53-binding sequence and a reporter gene are operably linked (hereafter called reporter vector in some cases); (b) measuring the expression level of the reporter gene; and (c) comparing the expression level of the reporter gene measured in step (b) to that measured in the absence of the test sample to select a compound capable of either decreasing or increasing the expression level.

The "p53-binding sequence" (BDS) used herein refers to the sequence to which the p53 protein binds to induce the transcription of "p53AIP1" gene, the target gene of p53 protein. A specific example of this sequence is 5'-TCT CTT GCC CGG GCT TGT CG-3' (SEQ ID NO: 8).

There is no particular limitation in the type of reporter genes used in this invention as long as their expression is detectable, and any reporter genes generally used in various assay systems by those skilled in the art can be employed. Preferable examples of the reporter gene include luciferase gene, chrolamphenicol acetyl transferase (CAT) gene, and β-galactosidase gene, but are not limited thereto.

Herein, that the p53-binding sequence and a reporter gene are "operably linked" in the above-described step (a) means that the binding sequence and reporter gene sequence are so linked that the binding of p53 to the p53-binding sequence triggers the induction of the reporter gene expression. Preferably, a minimal promoter sequence is arranged upstream of the reporter gene, and the p53-binding sequence further upstream of the promoter sequence.

The reporter vector of the present invention can be constructed by modifying the known expression vector suitable for the host cell used in the assay. For example, as shown in Example 3, it can be prepared by linking BDS (SV40-BDS) and the luciferase gene upstream of SV40 promoter in the pGL3 promoter vector.

There is no particular limitation in the type of cells transduced by the reporter vector, and, for example, H1299 cell line, SW480 large bowel cancer cell line;, and Saos2 osteosarcoma cell line can be used.

Cells can be transduced the reporter vector using a variety of methods known to those skilled in the art, including the above-described calcium phosphate precipitation method and electroporation method.

The expression level of reporter gene in the above-described step (b) can be measured by the methods generally used by those skilled in the art depending on the type of the reporter gene used. For example, in the case of using the luciferase gene as a reporter gene, the luciferase activity can be measured, as shown in Example 3, using a Dual Luciferase system (Promega) on the market.

Based on the result of the measurement of expression level of the reporter gene by the step (b), a compound that reduces or enhances the expression level of reporter gene compared to that measured by the similar method in the absence of the test sample, is selected. P53 is known to bind to the "p53-binding sequence", activate the transcription of target gene, and then induce apoptosis. Therefore, the compounds of this invention that reduce the expression level of the reporter gene are candidate compounds for an apoptosis inhibitor, while those that enhance the expression level of the reporter gene are candidate compounds for an apoptosis accelerator.

Examples of test samples include, as described above, cell extracts, expression products of a gene library, synthetic low molecular weight compounds, synthetic peptides, and natural compounds.

The presents inventors also found, as shown in Examples described below, that p53AIP1 of this invention interacted with bcl-2 protein in mitochondria, and demonstrated that this interaction influenced the p53AIP1-associated apoptosis mediated by the mitochondrial membrane potential, indicating that compounds that accelerate or inhibit the interaction between p53AIP1 and bcl-2 protein would have the function to control apoptosis. Therefore, the present invention provides a method of screening for candidate compounds for apoptosis controlling agents, which comprises the steps of: (a) contacting a test sample with the protein or peptide of this invention and bcl-2 protein; (b) measuring the binding activity of the protein or peptide to bcl-2 protein; and (c) selecting a compound that reduces or enhances the binding activity measured in the step (b) compared to that measured in the absence of the test sample.

Information on the nucleotide sequence of DNA (bcl-2 gene) encoding the bcl-2 protein is available from Genbank (Genbank accession No: M13994) and such.

In the screening method of the present invention, the above-described test samples can be used. The "contacting" in the above-described step (a) is usually carried out by adding a test sample to a solution containing the protein or peptide of this invention and bcl-2 protein, but not limited to this method. The solution containing the protein or peptide of this invention and bcl-2 protein can be prepared, for example, from extracts of cells transfected by the expression vector having DNAs encoding the protein or peptide. If the test sample is a protein, the above-described "contacting" may be conducted by co-transfecting cells with a DNA vector expressing the protein and another expression vector containing the DNAs encoding the protein of this invention and bcl-2 protein.

In addition, the protein of the present invention and bcl-2 protein used in the above-described screening method may be partial peptides of the proteins containing the amino acid regions involved in their interaction.

Those skilled in the art can conduct the measurement of binding activity described in the above-described step (b) by the immunoprecipitation method, immunostaining method, or such. For example, as shown in Example 9 described below, the measurement can be performed by the immunoprecipitation method using the antibody of this invention and mouse monoclonal anti-bcl-2 antibody. More specifically, immunoprecipitation is caused using the antibody of the present invention and anti-bcl-2 antibody from a solution of the above-described step (a) in which a test sample is contacted with the protein or peptide of this invention and bcl-2 protein. Next, whether the precipitated immune complex contains both the protein of this invention and bcl-2 protein or not is assessed by Western blotting. When both proteins are contained, it is determined that the protein of this invention and bcl-2 protein have the activity to bind each other.

Alternatively, the binding activity described in the above-described step (b) can be measured by the two-hybrid method using yeast, in vitro binding experiment method using a recombinant protein biosynthesized in *Escherichia coli* or a protein synthesized in the in vitro protein synthesis system using the in vitro translation system, and such, as well as immunoprecipitation methods and immunostaining methods.

When the binding activity thus measured is lower than that measured in the absence of a test sample, the test sample is a candidate compound for an apoptosis inhibitor, while, when higher, it is a candidate compound for an apoptosis accelerator.

When the protein or antibody of the present invention, or the compound isolated by the screening method of this invention are used as drugs, they may be administered as such to patients, and also they may be administered as dosage forms prepared by drug manufacturing methods well-known in the art. For example, the dosage forms may be prepared by appropriately combining above-described protein, antibody, and compound with pharmaceutically acceptable carriers or media, such as sterilized water, physiological saline, plant oil, emulsifiers, suspending agents, surfactants, and stabilizers. Administration to patients may be carried out by methods known to those skilled in the art, for example, by intraarterial, intravenous, and subcutaneous injections, or by intranasal, transbronchial, intramuscular, or oral administration. Although the dosage may vary depending upon the body weight and age of patients and routes of administration, those skilled in the art can appropriately select a suitable dosage. In addition, when the compound can be encoded by DNA, gene therapy can be performed using a vector for gene therapy into which the DNA has been introduced. The dosage and method of administration may vary depending on the body weight, age, symptoms, and such of patients, those skilled in the art may select appropriate ones.

BRIEF DESCRIPTION OF THE DRAWINGS

FIG. 3 shows predictive amino acid sequences of p53AIP1α (SEQ ID NO: 2), β (SEQ ID NO: 4), and γ (SEQ ID NO: 6). Identical amino acid residues are shown on black background.

FIG. 6 presents photographs showing the localization of p53AIP1 in COS-7 cells. COS-7 cells were transfected with a plasmid DNA designed to express HA-tagged p53AIP1α (pCAGGS/N-HA-p53AIP1α). The cells were double-stained with anti-HA antibody (FITC-labeled) and anti-human mitochondria antibody (rhodamine-labeled).

FIG. 9 presents photographs showing the induction of apoptosis by ectopic expression of p53AIP1α. T98G cells were transfected with either pCAGGS/N-HA-p53AIP1α, or wild-type p53 or mutant (R273H) p53 expression vector. Expression of p53AIP1α or that of wild-type and mutant p53 were detected by anti-HA antibody or anti-p53 antibody, respectively. Apoptosis was detected by TUNEL method utilizing FITC emission.

BEST MODE FOR CARRYING OUT THE INVENTION

This invention is specifically illustrated below with reference to Examples, but it is not to be construed as being limited thereto.

EXAMPLE 1

Isolation of a Novel p53-inducible Transcription Unit

Figure 1:
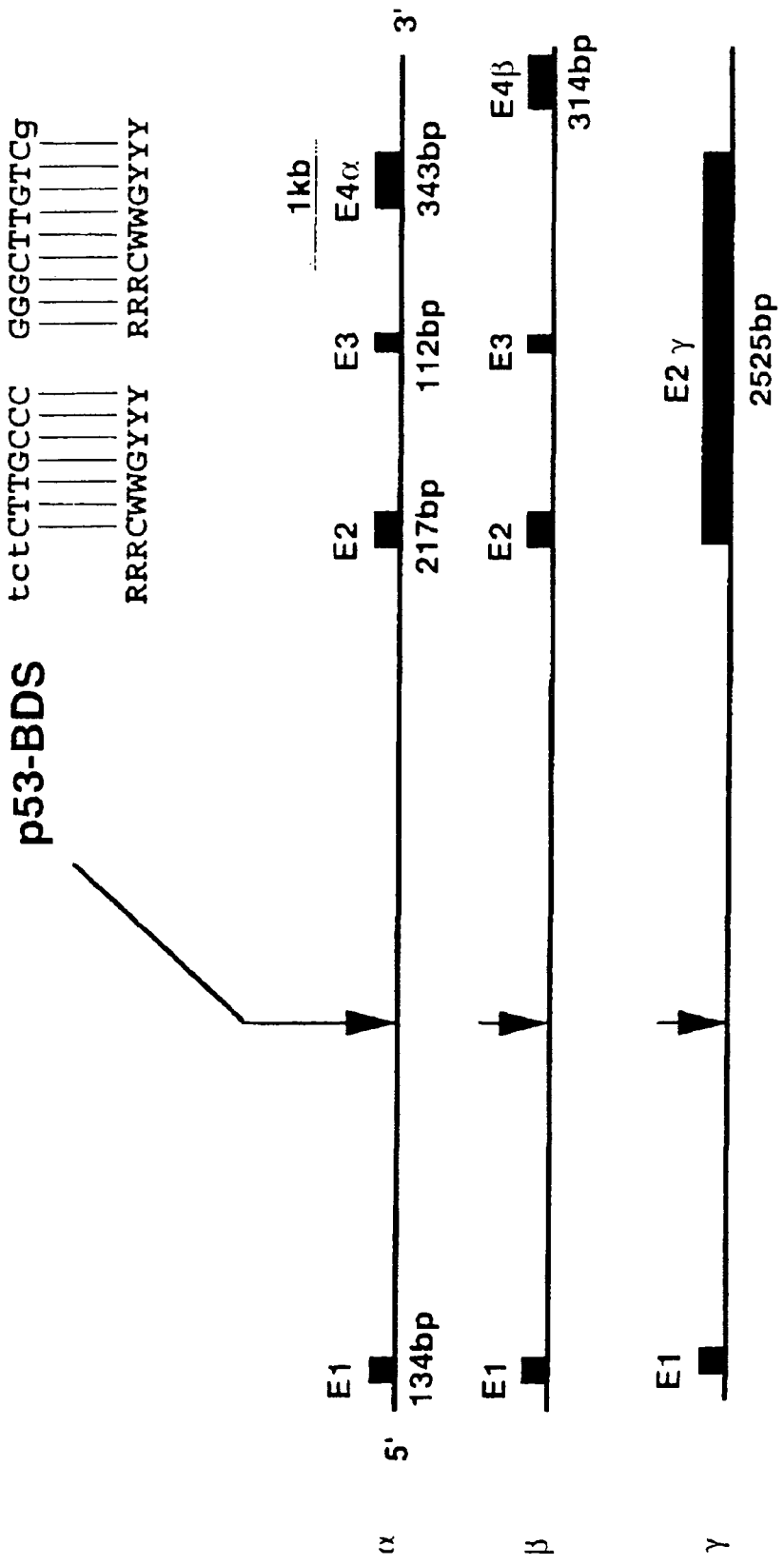
FIG. 1 shows the genomic structure of the p53AIP1 gene. The organization of exon-intron and transcripts of the p53AIP1 gene are presented. A potential p53 binding site (p53-BDS, SEQ ID NO: 8) is identified in intron 1. The sequence of the potential p53-binding site is compared with the consensus sequence (SEQ ID NO: 32). Nucleotides in uppercase represent identical nucleotides between the genomic sequence and the consensus sequence, and those in lowercase represent unmatched nucleotides. (R)=purine; (Y)=pyrimidine; (W)=A or T.

The present inventors isolated a number of human genomic sequences, whose transcription was presumably activated by p53, using a yeast enhancer trap system (p53-target site; Tokino et al. Hum. Mol. Genet. 3: 1537-1542, 1994). The inventors determined the nucleotide sequence of a 190-bp DNA fragment, corresponding to one of the above-described sequences (clone TP53-41 in Tokino et al., Hum. Mol. Genet. 3: 1537-1542, 1994), and found a putative p53-binding sequence (BDS) within the fragment (FIG. 1). To isolate a larger genomic region comprising the fragment, the 190-bp DNA fragment comprising a p53-target site was radiolabeled, and used as a probe for screening a human cosmid library consisting of $10^6$ colonies. A cosmid designated as TP53-cos38 was isolated by the screening, and then subjected to FISH analysis. FISH analysis was performed using the cosmid clone TP53-cos38 as a probe according to the method described in Inazawa et al., Genomics 17: 153-162, 1993. To prepare denatured G banding pattern, human metaphase chromosomes were prepared by the thymidine synchronization/bromodeoxyuridine release technique. Before hybridization, cells at M phase were stained with Hoechst 33258, and subjected to UV irradiation. The probe was labeled with biotin-16-dUTP (Boehringer) by nick translation and hybridized with denatured metaphase chromosomes. The hybridization signals were detected with FITC-avidin (Boehringer). Precise assignment of hybridization signals was achieved by visualizing the replicated G bands.

As a result, TP53-cos38 was found to be mapped to chromosome 11q24 (data not shown). The entire 40-kb genomic sequence in cos38 was determined by shot-gun sequencing. The 40-kb sequence in cos38 was searched for predicted exons using two exon-predicting computer programs, Grail2 (Solovyev et al., Nucleic Acids Res. 22: 5156-5163, 1994), and GENSCAN (Burge and Karlin, J. Mol. Biol. 268: 78-94, 1997) Analysis with the Grail2 program predicted 12 possible exons with "excellent" or "good" scores; the GENSCAN program also predicted 12 possible exons. Among them, four were predicted as candidate exons by both programs. Hence, a total of 20 candidate exonic segments were present in the vicinity of putative p53-binding sequences.

Oligonucleotides corresponding to the candidate exons were synthesized, and exon connection experiments were performed using cDNA that were reverse transcribed from thymus mRNA. As a result, 474-bp cDNA fragment consisting of the two predicted exons was prepared (data not shown).

EXAMPLE 2

Isolation of the p53AIP1 Gene

In order to isolate a full length cDNA of the above-described DNA fragment, glioma cells, U373MG, were infected for 48 hr with a replication-defective adenovirus expressing wild-type p53 (Ad-p53), and then poly(A)+RNA was isolated from resulting cells. Northern blotting analysis using the 474-bp cDNA fragment as a probe was performed as follows.

Poly(A)+RNA (3 µg) extracted from U373MG cells infected with Ad-p53 was separated by electrophoresis on a 1% agarose gel containing 1×MOPS and 2% formaldehyde, and transferred to a nylon membrane. The RNA blot was hybridized with a random-primed $^{32}$P-labeled p53AIP1 cDNA probe or β-actin in 5×SSPE/10×Denhardt's/2% SDS/50% formamide at 50° C., washed in 0.1×SSC/0.1% SDS at 65° C., and then subjected to autoradiography at −80° C.

Figure 2:
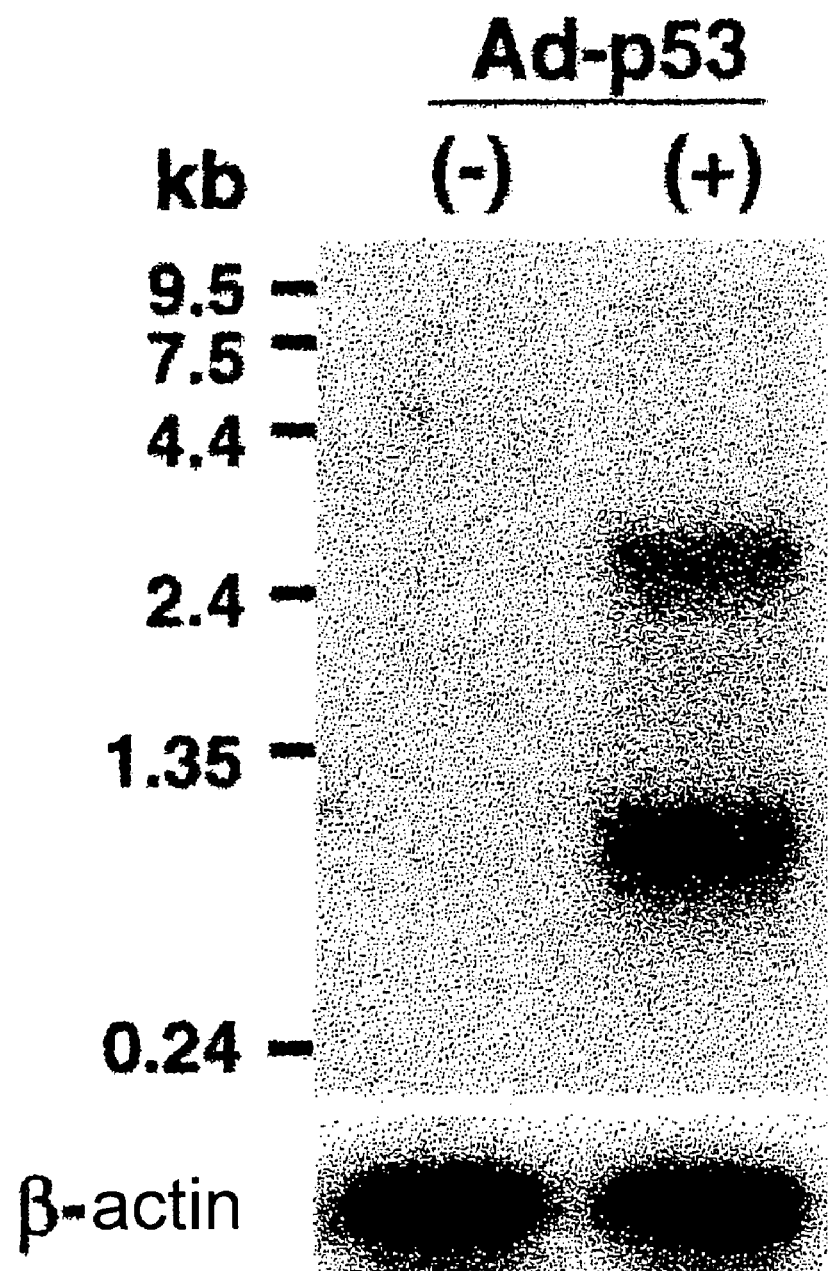
FIG. 2 is a photograph showing the induction of p53AIP1 by p53. Northern blotting was performed using 3 µg of poly (A)+RNA isolated from U373MG cells infected with Ad-p53 for 48 hr. Autographs of the Northern blotting performed with p53AIP1 and β-actin probes are shown.

The analysis detected 0.8-kb and 2.7-kb transcripts whose transcription were strongly induced in U373MG cells by infection with Ad-p53 (FIG. 2). Northern blotting analysis using mRNAs from 16 normal human tissues revealed expression of the gene only in thymus (data not shown).

Next, a CDNA library was constructed by using the poly (A)$^{30}$ RNA (2 µg) derived from U373MG cells which was infected with a recombinant adenovirus vector comprising wild-type p53 (Ad-p53) for 48 hr. $10^6$ independent colonies in the library was screened using a 474-bp p53AIP1 cDNA fragment, the exon-connected PCR products, as a probe, and then 20 positive clonesof p53AIP1 gene were obtained. Sequencing of these cDNA clones identified three major transcripts, designated as α, β, and γ, which consisted of 806, 777, and 2659 nucleotides with open reading frames encoding 124, 86, and 108 amino acids, respectively (FIG. 3). Computer analysis using the FASTA (Pearson, Methods Enzymol. 183: 63-98, 1990) and BLAST (Altschul et al., J. Mol. Biol. 215: 403-410, 1990) programs detected no significant homology between these three products and any known protein in the public database. A comparison of genomic and cDNA sequences determined the genomic structure of this novel gene, designated p53AIP1 on the basis of the functional characteristics described later. The gene spans an 8.2-kb genomic region, and contains five exons (FIG. 1). The nucleotide sequence of this gene is shown in SEQ ID NO: 7. The three transcripts are generated by alternative splicing. That is, it was found that exon 2 of p53AIP1γ includes introns 2 and 3 of p53AIP1α and that the above-described 190-bp genomic fragment comprising a putative p53-binding site was found within intron 1.

EXAMPLE 3 p53AIP1 as a Novel Target-Molecule for p53

In order to determine whether p53 was able to bind to oligonucleotides corresponding to the BDS sequence in intron 1 of the p53AIP1 gene, electrophoretic mobility shift assay (EMSA) was performed as described below. First, the following oligonucleotides were designed:

```
                                    (oligomer 1S, SEQ ID NO:9)
5'-TCTCTTGCCCGGGCTTGTCG-3';

(oligomer 1A, SEQ ID NO:10)
5'-CGACAAGCCCGGGCAAGAGA-3'.
``` and

Next, the oligomers 1S and 1A were annealed, and labeled with [γ-$^{32}$P] DATP. H1299 lung carcinoma cells (obtained from ATCC) were infected-with Ad-p53. Nuclear extracts were prepared from these cells, and incubated with 0.5 µg of sonicated salmon sperm DNA, EMSA buffer (consisting of 0.5×TBE, 20 mM HEPES (pH 7.5), 0.1 M NaCl, 1.5 mM MgCl$_2$, 10 mM dithiothreitol, 20% glycerol, 0.1% NP-40, 1 mM PMSF, 10 µg/ml pepstatin, and 10 µg/ml leupeptin), and the $^{32}$P-labeled double-stranded oligomers for 30 min at room temperature. In some cases, the nuclear extracts were incubated with monoclonal anti-p53 antibodies, PAb421 (Oncogene Science) and PAb1801 (Santa Cruz Biotechnology). After incubation, the mixture was separated by electrophoresis on a 4% undenatured polyacrylamide gel containing 0.5× TBE. The gel was then dried and, subjected to autoradiography for 3 hr at −80° C.

Figure 4:
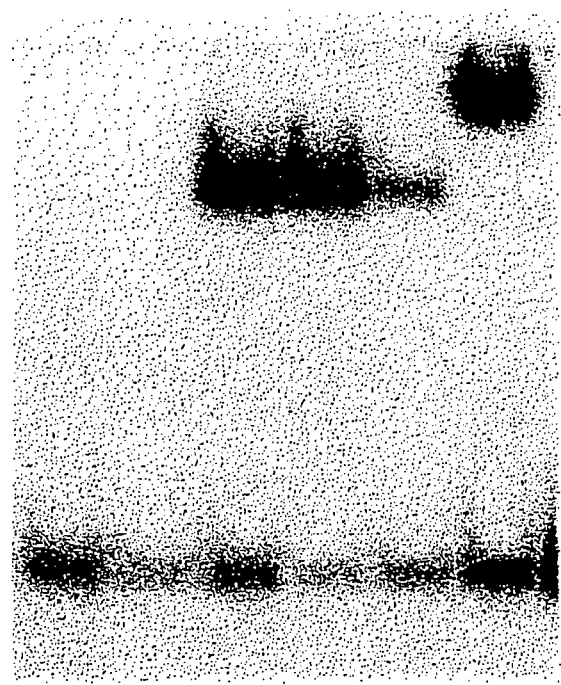
FIG. 4 shows the result of EMSA. Anti-p53 antibodies, pAb421, and pAb1801, were included in the indicated lanes. The p53-DNA interaction was inhibited by unlabeled oligonucleotides corresponding to the binding site of the p53AIP1 gene (Self), but not by the nonspecific oligonucleotides (TL).

As shown in FIG. 4, the result showed that the BDS sequence binds to a molecule in the nuclear extracts of lung cancer cells H1299 infected with Ad-p53. When anti-p53 antibodies (PAb421 and/or PAb1801) were added to the mixture, additional shifted bands were observed. Unlabeled oligonucleotide itself but not a random oligonucleotide, inhibited the interactions. The result suggested that p53 protein could indeed bind to BDS in vitro.

To further evaluate the transcription-enhancing activity of the binding sequences, a reporter assay was performed with the luciferase gene linked to one (p53BDS (1×)) or two copies (p53BDS (2×)) of p53BDS upstream of the SV40 promoter (SV40-BDS) of the pGL3 promoter vector as described below.

Human WAF1-luciferase plasmid was obtained from Mr. Ikawa (Osada et al., Nature Med. 4: 839-843, 1998). The p53-AIP1 reporter constructs were made as follows. For construction of p53BDS plasmid, two oLigonucleotides, 5'-CTCTCTTGCCCGGGCTTGTCGGTAC-3' (SEQ ID NO: 11) and 5'-CGACAAGCCCGGGCAAGAGAGGTAC-3' (SEQ ID NO: 12), were designed. The oligomers were annealed, and subcloned into the KpnI site of the promoter of pGL3 vector (Promega, Madison, Wis., USA). For each transfection, 0.3 µg of -reporter plasmid and 50 ng of an expression vector for either wild-type p53 or mutant p53 were cotransfected with 0.3 µg of pRL-TK vector into H1299 cells. After 24 hr, cells were washed with PBS, and lyzed in 500 µl of passive lysis buffer (Promega). The Dual Luciferase system (Promega) was used for measurement of the activities of firefly and sea pansy luciferases. Quantitation of the activities of both luciferases and calculation of relative activities were performed using a luminometer mainly. The experiment was repeated at least three times, and means and standard deviations were calculated.

Figure 5:
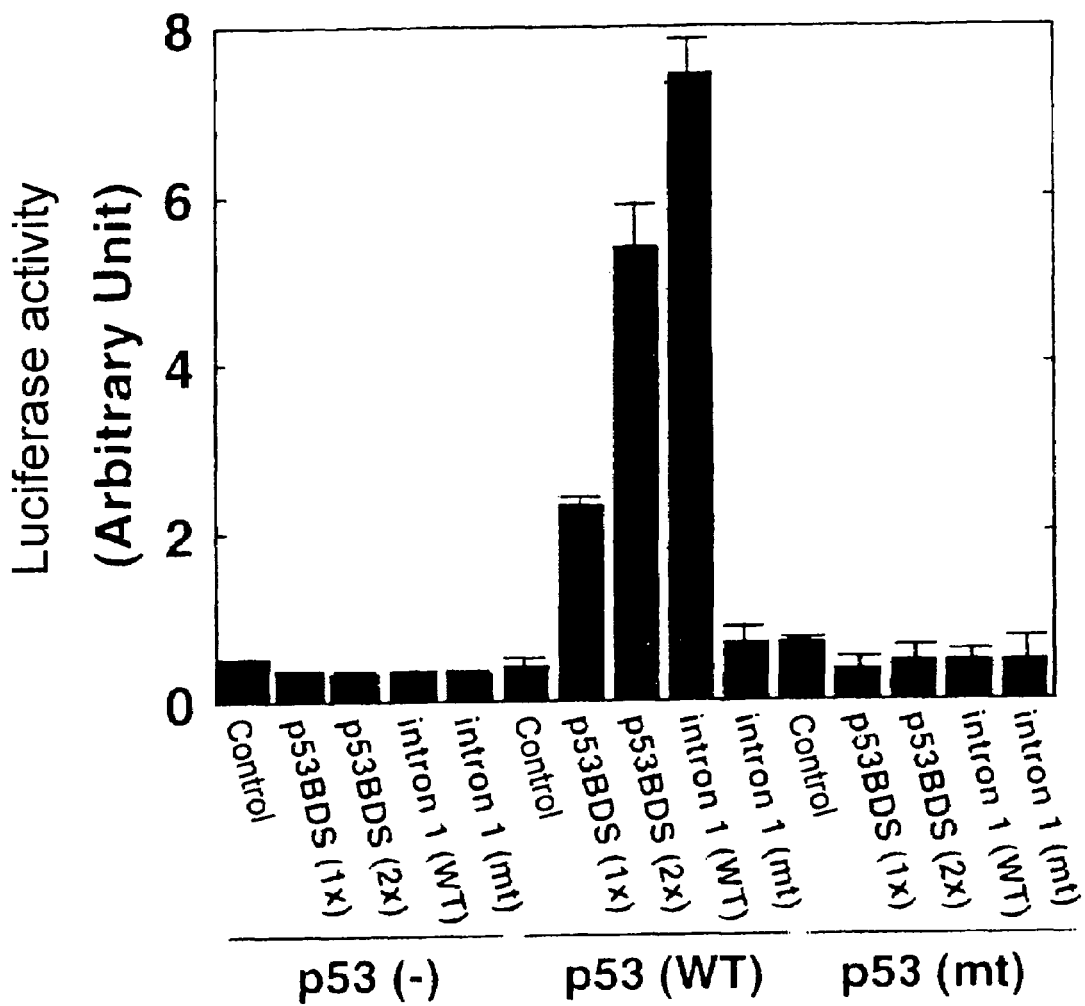
FIG. 5 is a graph showing p53-responsive p53BDS. Reporter constructs comprising one or two copies of the p53BDS (pS3BDS (1×) or p53BDS (2×), respectively), or 500 bp genomic sequence in intron 1 (intron 1-wt or intron 1-mt) were prepared. A point mutation of the fourth nucleotide C to T within the p53BDS was introduced into the 500 bp genomic sequence (intron 1-mt). The activity is represented as a relative value of measured luminescence from sea pansy luciferase to measured luminescence from firefly luciferase from cotransfected pRL-TK (internal control). Mean values of the results of three experiments are shown with error bars of standard deviations.

Transfection of p53BDS (1×), p53BDS (2×), or control (SV40 promoter without a p53 binding site) vector into a colon cancer cell line "SW480" (obtained from ATCC) lacking wild-type p53 did not enhance luciferase activity. However, cotransfection of p53BDS (1×) or p53BDS (2×) with the expression plasmid designed to express wild-type p53 increased luciferase activity significantly, whereas cotransfection with the mutant p53 expression vector failed to so increase luciferase activity (FIG. 5).

Next, a heterogeneous reporter vector (intron 1-wt or intron 1-mt) was constructed as follows. A 500-bp segment (intron 1-wt), or mutant 500-bp segment (intron 1-mt) corresponding to intron 1 of the p53AIP1 gene containing a wild-type or mutated p53BDS sequence was cloned upstream of the SV40 minimal promoter. Intron 1-wt or intron 1-mt reporter vector was cotransfected with either wt-p53 or mt-p53 expression vectors into SW480 cells. Luciferase activity of intron 1-wt, but not intron 1-mt, was increased by cotransfection with the wt-p53 expression vector (FIG. 5). Moreover, mt-p53 enhanced luciferase activity of intron 1-wt reporter vector (FIG. 5). These results indicate that the binding site activates transcription p53-dependently, and therefore p53AIP1 is a direct targeting gene of p53 protein.

EXAMPLE 4

Intracellular Localization of p53AIP1

The PSORT motif prediction program (Nakai and Kanehira, Genomics 14: 897-911, 1992) indicated the presence of a mitochondrial targeting sequence at the N-termini of p53AIP1α and p53AIP1β, suggesting that p53AIP1 might be a mitochondrial protein. Thus, the intracellular localization of p53AIP1 was analyzed as follows.

First, a plasmid clone, pCAGGS/C-HA-p53AIP1α, was constructed to express p53AIP1α with an HA tag at the C-terminus. COS-7 cells were transfected transiently with pCAGGS/C-HA-p53AIP1α, and placed on a multi-well chamber slide (Beckton Dickinson) coated with poly-P-lysine. Then, the cells were fixed with 4% paraformaldehyde in PBS, and permeabilized with 0.1% Triton X-100 in PBS at 4° C. for 3 min. The cells were blocked in blocking solution (3% BSA in PBS) at room temperature for 60 min. The cells were then incubated with rat anti-HA antibody, 3F10 (Boehringer, 1000 times diluted with blocking solution), and mouse anti-human mitochondrial antibody (Leinco Technologies, Inc., 500 times diluted with blocking solution) at room temperature for 2 hr. The rat anti-HA and mouse anti-human mitochondrial antibodies were stained with FITC-conjugated goat anti-rat secondary antibody and rhodamine-conjugated goat anti-mouse secondary antibody, respectively, and then observed with an ECLIPSE E600 microscope (Nikon).

As shown in FIG. 6, p53AIP1α was stained strongly in the perinuclear region, and stained as a punctated pattern in the cytoplasm. When mitochondria was stained using the anti-mitochondrial antibody, the green signal of p53AIP1 coincided exactly with the red signal of mitochondria. This result revealed a mitochondrial location of p53AIP1 protein.

EXAMPLE 5

Induction of Endogenous p53AIP1 by DNA Damage

Considering that p53AIP1 is induced by wild-type p53, the present inventors examined whether expression of p53AIP1 could be induced by DNA-damaging treatment through γ-ray irradiation or exposure to adriamycin in either newborn skin-derived normal human fibroblast (NHDF) cells (Clonetics Inc.) with wild-type p53,or SW480 without wild-type p53. DNA-damaging treatment was performed as follows.

Cells were inoculated 24 hr before treatment, and grown to 60% to 70% confluency. NHDF and SW480 cells were continuously treated with adriamycin (doxorubicin) at a concentration of 0.2 µg/ml or were treated with γ-ray irradiation at about 1 Gy/min (14 Gy).

Figure 7:
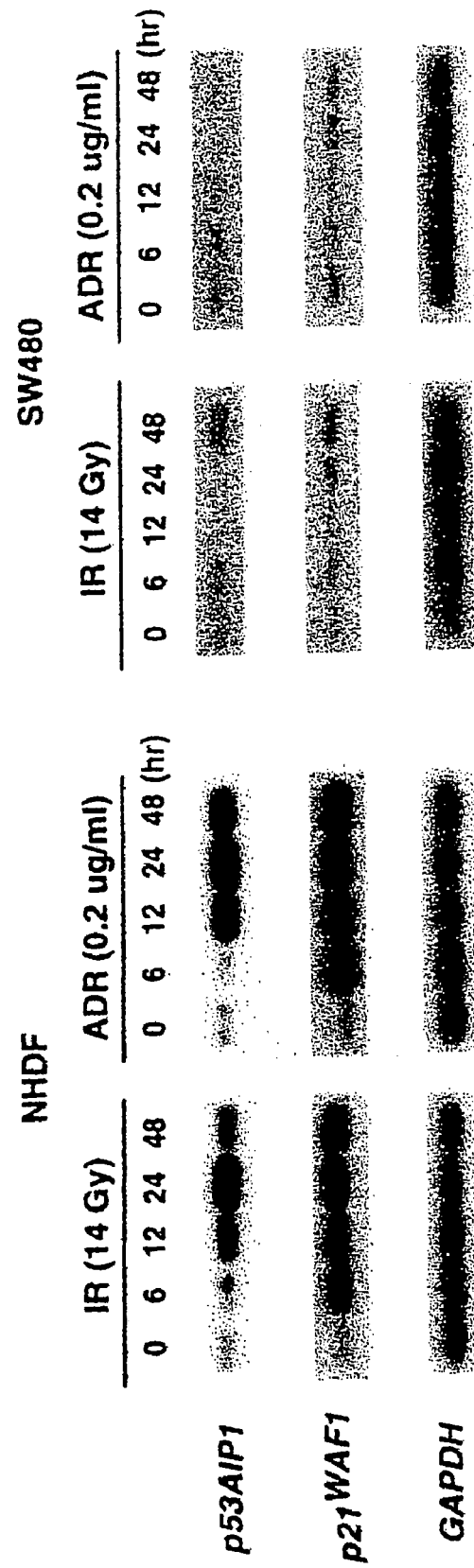
FIG. 7 represents photographs showing the induction of endogenous p53AIP1 mRNA by DNA damages in human cells. Results of RT-PCR experiments under the genotoxic stresses are shown. Expression of the GAPDH gene was determined as a quantity control. p53AIP1 and p21/WAF1 expression induced by γ irradiation (IR) and adriamycin treatment (ADR) is analyzed. NHDF is a normal human dermal fibroblast cell line containing the wild-type p53 gene; SW480 is a colorectal adenocarcinoma cell line lacking the wild-type p53 gene.

As a result, DNA damage from genotoxic agents strongly induced transcription of p53AIP1 in NHDF cells but not in SW480 cells (FIG. 7). While p21$^{Waf1}$ expression in NHDF cells reached a maximum after 6 hr of exposure to either adriamycin or ionizing radiation, induction of maximum levels of p53AIP1 were observedonly at 24 hr after exposure. These results suggest that although p53AIP1 is induced in response to DNA damage, the molecular mechanism for its induction is quite different from that of p21$^{Waf1}$.

EXAMPLE 6

Induction of Apoptosis by Dissipation of Mitochondrial ΔΨm Mediated by p53AIP1

In order to test whether p53AIP1 itself functions as a growth suppressor, colony formation assays were performed. First, mammalian expression vectors (pCAGGS/N-HA-p53AIP1α, β, and γ) containing the entire encoding sequence of each transcript were constructed as follows.

The entire coding sequence of cDNAs (p53AIP1α, β, and γ) were amplified by PCR under conditions of 94° C. for 2 min, 25 cycles of 94° C. for 30 sec, 56° C. for 30 sec, and 72° C. for 30 sec, and finally 72° C. for 5 min, using pfu DNA polymerase (Stratagene) and following primers:

```
Primers for p53AIP1-α amplification
α, β, γ-F:   5'-ATG GGA TCT TCC TCT GAG GCG AGC-3';   (SEQ ID NO:13)
and

α-R:         5'-TCA CTG CAA CCT CAA CGG TGC TTT-3';   (SEQ ID NO:14)

Primers for p53AIP1-β amplification
α, β, γ-F:   5'-ATG GGA TCT TGA GGC GAG CTC CTC-3';   (SEQ ID NO:15)
and

β-R:         5'-TCA CTG CAA CCT CAA CGG TGC TTT-3';   (SEQ ID NO:16)

Primers for p53AIP1-γ amplification
α, β, γ-F:   5'-ATG GGA TCT TCC TCT GAG GCG AGC-3';   (SEQ ID NO:13)
and

γ-R:         5'-TCA GTT CCC AGC TCT GTC CAA TGC-3'.   (SEQ ID NO:17)
```

Next, the PCR products were inserted into the unique EcoRI site of the-pOAGGS mammalian expression vector, which contains a CAG (cytomegalovirus immediate early enhancer chicken β-actin hybrid) promoter (Niwa et al., Gene 108: 193-199 (1991)). Hemagglutinin (HA) epitope tag was placed at the N-terminus (pCAGGS/N-HA-p53AIP1α, β, and γ) or C-terminus (pCAGGS/C-HA-p53AIP1α, β, and γ) of each expression vector. The constructs were confirmed by sequencing.

Then, immunoblotting using rat anti-HA tag monoclonal antibody (3F10, Boehringer) was performed to confirm that each vector was expressed in mammalian cells (data not shown). To confirm geneticin resistance, the pcDNA3.1(+) vector (Invitrogen) comprising a neomycin (G418) resistant gene was cotransfected with eitherthep53AIP1 expression vector (pCAGGS/N-HA-p53AIP1α, β, and γ) or pCAGGS vector alone into 2×10⁵ glioma cell line T98G cells (obtained from Human Science Research Resource Bank (Japan)) lacking wild-type p53. Transfection was performed according to the instructions from the manufacturer. Twenty hours after transfection, cells were diluted four times, and cultured in the presence of 600 μg/ml geneticin (G418) for 2 weeks. Three transfections were performed separately, and the numbers of resulting colonies were counted for each time (Furuhata et al., Oncogene 13: 1965-1970, 1996).

Figure 8:
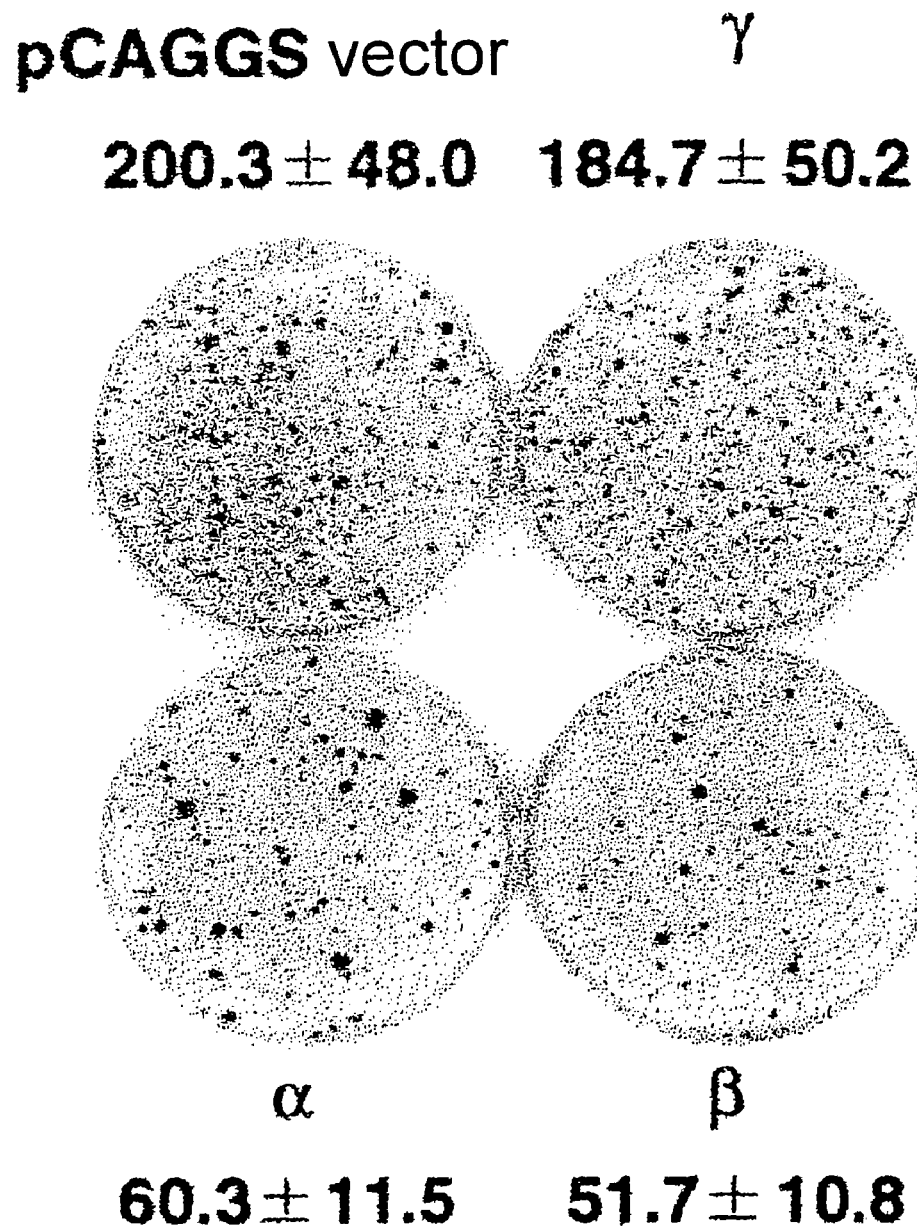
FIG. 8 is a photograph showing growth-suppressing effect of T98G cells by ectopic expression of p53AIP1. Expression vectors for HA-tagged p53AIP1α, β, and γ (pCAGGS/N-HA-p53AIP1-α, β, and γ) and mock vector (pCAGGS) were cotransfected with pcDNA3.1(+) vector in T98G cells, and resulting cells were cultured in the presence of 600 µg/ml of geneticin for 2 weeks.

As shown in FIG. 8, the introduction of pCAGGS/N-HA-p53AIP1α or β resulted in substantial growth suppression, as seen by a 3- to 4-fold decrease in the number of geneticin-resistant colonies. Growth suppression was also observed when HA tag was inserted into the C-terminus of the pCAGGS vector (pCAGGS/C-HA-p53AIP1α or β; data not shown). The present inventors failed to establish a stable transformant overexpressing p53AIP1 because of the cytotoxicity observed in the colony formation assays.

In view of the above observations, a late induction by p53, growth-suppressing activity, and mitochondrial localization, suggest that p53AIP1 might play an important role in p53-dependent apoptosis. To investigate whether introduction of exogenous p53AIP1 could indeed induce apoptotic cell death, in situ terminal transferase-mediated dUTP nick end-labeling (TUNEL) analysis was performed. First, T98G cells were transfected with the p53AIP1 expression vector (pCAGGS/N-HA-p53AIP1-α) or p53 expression vector (wild-type or mutant), and then harvested after 48 hr. TUNEL analysis was performed using Apotag Direct (INTERGEN) according to the manufacturer's instructions. Then, immunofluorescent staining was performed using rat anti-HA tag antibody, 3F10 (Boehringer), or monoclonal p53 antibody, Ab-6 (Oncogene Science). The primary antibody was stained with rhodamine-conjugated secondary antibody, and the samples were observed using an ECLIPSE E600 microscope (Nikon). DNA fragments were evaluated using the ApoAlert LM-PCR ladder assay kit (Clontech) according to the manufacturer's instructions.

The results of TUNEL analysis showed that more than half of the T98G cells expressing p53AIP1α underwent apoptosis. As a control, T98G cells were transfected with a wild-type p53 or amutant p53 (p53-R273H) expression vector. Introduction of exogenous wild-type p53 also caused apoptotic cell death, but TUNEL-positive cells were significantly fewer in cultures of cells that were transfected with the plasmid DNA designed to express mutant p53 (FIG. 9). Transfection with pCAGGS vector alone did not induce apoptotic cell death (data not shown).

To investigate the mechanism by which p53AIP1 induces apoptosis, the mitochondrial ΔΨm, an indicator of electrochemical gradient across the mitochondrial inner membrane, was examined using Mitotracker CMXRos (Molecular Probes).

To evaluate the mitochondrial membrane potential, cells were incubated in culture media containing 70 mM Mitotracker Red CMXRos (Molecular Probes) at 37° C. for 30 min, and then fixed to be labeled with a longer wavelength (579 nm to 599 nm) fluorescence emission.

Figure 10:
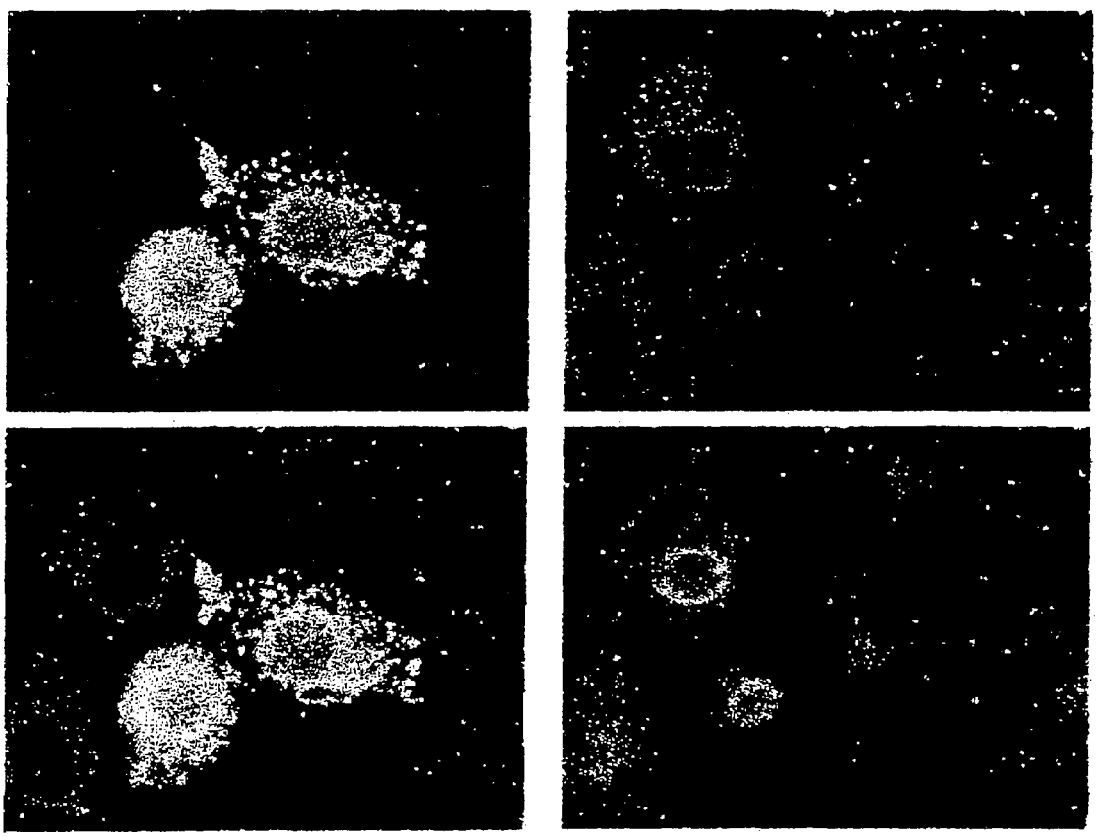
FIG. 10 presents photographs showing the p53AIP1α-induced dissipation of mitochondrial ΔΨm. Upper left: Expression of p53AIP1α was detected by anti-HA antibody (green). Upper right: Mitochondrial ΔΨm was stained by MitoTracker Red CMXRos (red). Lower left: Merged image of ectopically expressed p53AIP1α protein and mitochondrial ΔΨm. Lower right: Merged image of DAPI and mitochondrial ΔΨm.

Almost all cells expressing p53AIP1α revealed dissipation of mitochondrial ΔΨm at 24 hr after transfection (FIG. 10).

To investigate the in vivo effect of p53AIP1, the present inventors designed adenovirus vectors expressing p53AIP1α and β (Ad-p53AIP1α and β). Ad-p53AIP1α or β, or Ad-LacZ were infected into T9-8G cells, and FACS and TUNEL assays were performed at 72 hr after infection. Apoptosis was detected by FACS and TUNEL assays as well as the DNA ladder assay using LM-PCR. For FACS analysis, adherent and detached cells were combined at 36 hr after DNA damage, and fixed overnight with 75% ethanol in PBS at 4° C. After rinsed twice with PBS, cells were incubated at 37° C. for 30 min with 1 ml of PBS containing 1 mg of boiled RNase. Cells were then stained in 1 ml of PBS containing 10 μg of propidium iodide. A total of $2\times10^4$ cells were analyzed in a flow cytometer (FACScalibur; Becton Dickinson).

Figure 11:
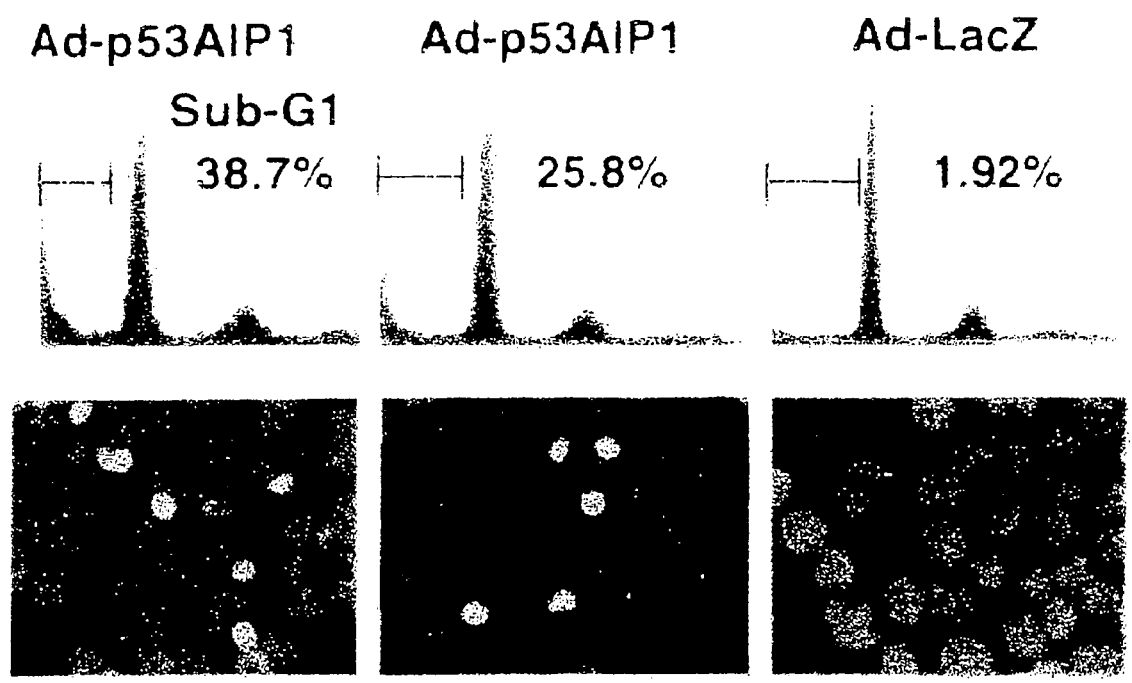
FIG. 11 presents diagrams and photographs both showing the function of p53AIP1 in p53-induced apoptosis. Ad-p53AIP1α and β but not Ad-LacZ induce apoptosis in T98G cells. In T98G cells infected with Ad-p53AIP1αand β, r Ad-LacZ, apoptotic cells were evaluated by FACS and TUNEL analyses at 72 hr after infection.
Figure 12:
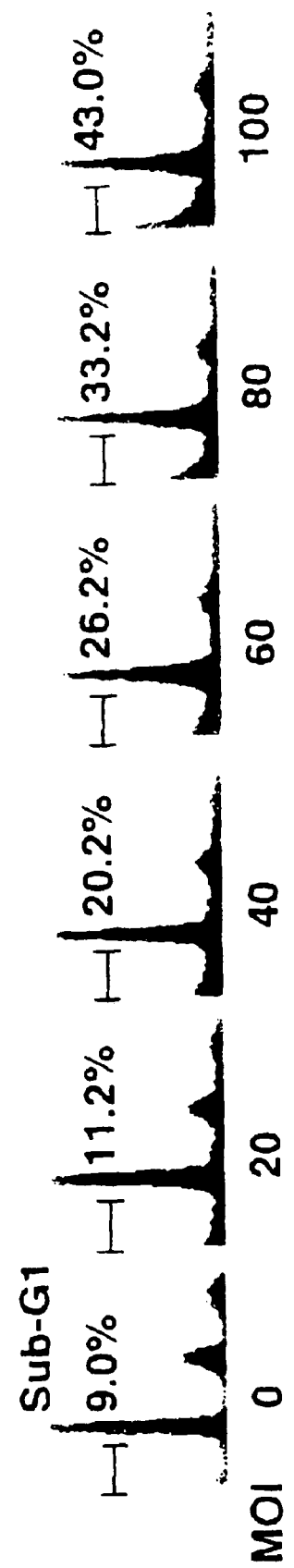
FIG. 12 shows the function of p53AIP1 in p53-induced apoptosis. Apoptosis of T98G cells was induced by infection with Ad-p53AIP1α in a dose-dependent manner. In T98G cells infected with various doses of Ad-p53AIP1α, apoptotic cells were evaluated by FACS analysis at 72 hr after infection.

The results showed that an introduction of Ad-p53AIP1α and β, but not an introduction of Ad-LacZ, into T98G cells induces apoptosis (FIG. 11). Moreover, apoptotic cell death was induced by Ad-p53AIP1α in a dose-dependent manner (FIG. 12). Next, the present inventors examined whether inhibition of endogenous p53AIP1 could block p53-dependent apoptosis induced by infection of Ad-p53. To inhibit endogenous p53AIP1 expression, antisense oligonucleotides (AS1: GATCCCATCCAGGGGA/SEQ ID NO: 18) and a control sense oligonucleotides (SE1: GGAGGCAGGTGAGGAG/ SEQ ID NO: 19) were prepared using the nucleotide sequence of the p53AIP1, and purified by HPLC. FITC-labeled AS was used for evaluation of nuclear incorporation efficiency. Cells were transfected with antisense oligonucleotides (1 μM) using Lipofectin reagent (GIBCO-BRL) for 4 hr, and then infectedwith either Ad-p53 or Ad-LacZ. Forty-eight hours after infection, apoptotic cells were analyzed by FACS analysis.

Figure 13:
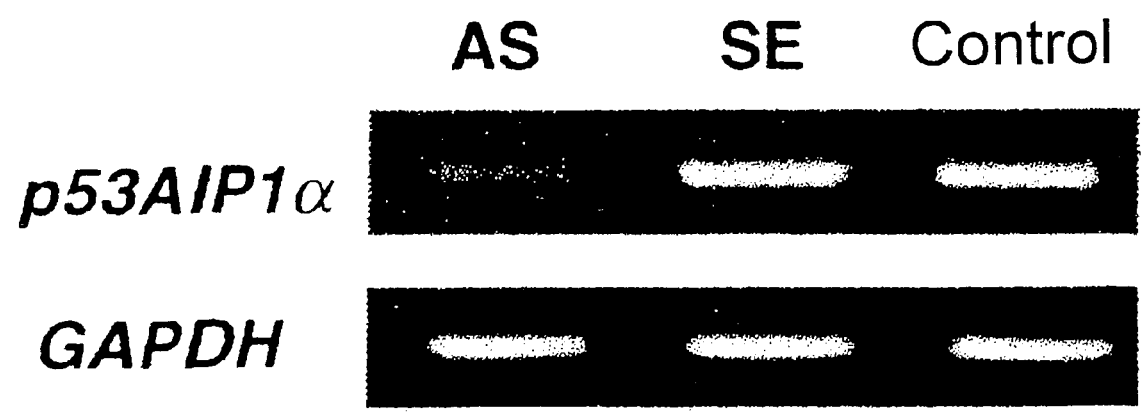
FIG. 13 presents photographs showing the function of p53AIP1 in p53-induced apoptosis. Inhibition of p53AIP1α mRNA expression by antisense oligonucleotide is shown. U373MG cells were transfected with antisense oligonucleotides (AS) or sense oligonucleotides (SE) (1 µM) using Lipofectin reagent (GIBCO-BRL) for 4 hr, and then the cells were infected with Ad-p53. Forty-eight hours after infection, RNA was isolated, cDNAs were synthesized, and p53AIP1α expression was examined by RT-PCR.
Figure 14:
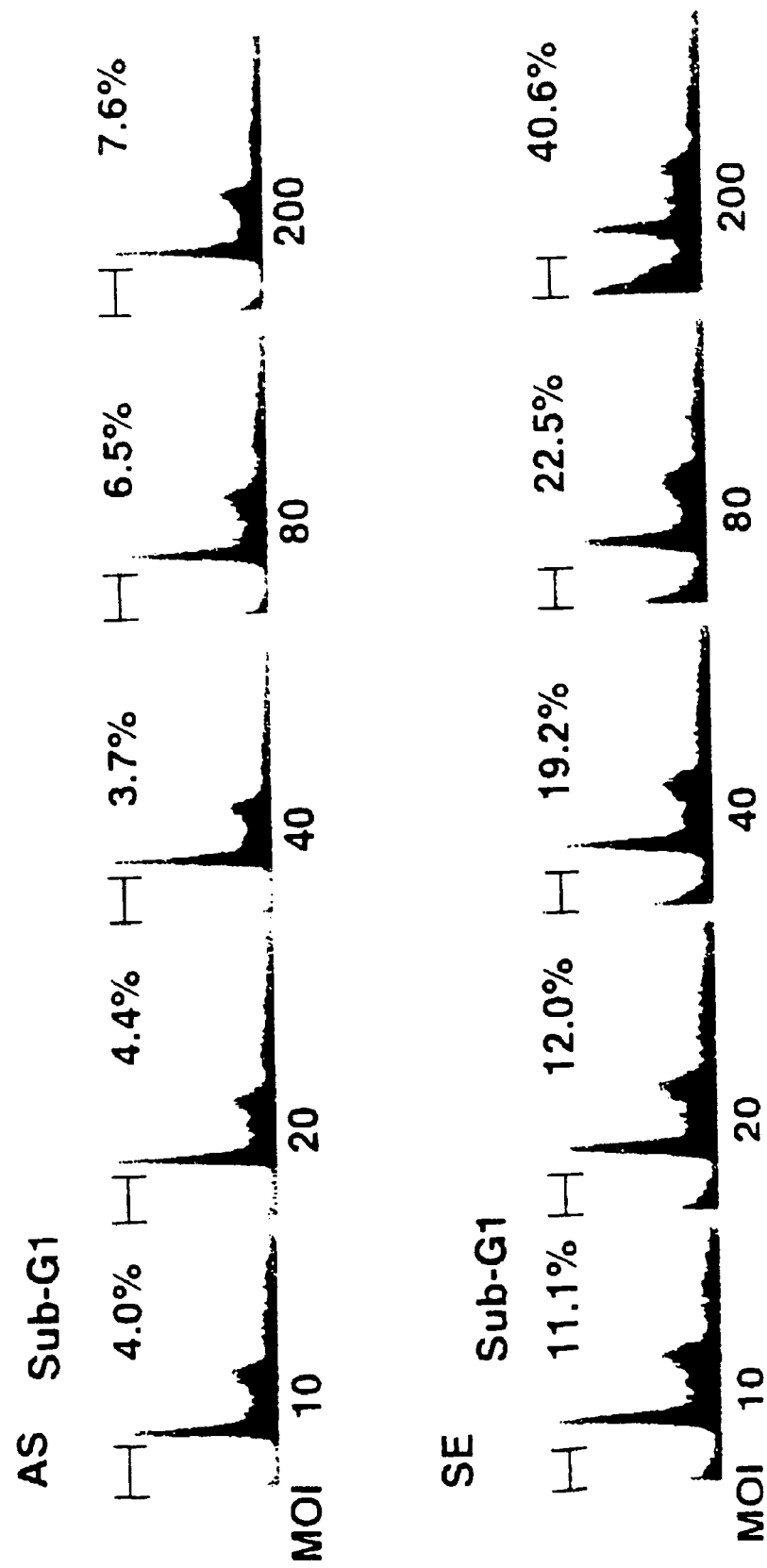
FIG. 14 shows the function of p53AIP1 in p53-induced apoptosis. Inhibition of p53AIP1α expression blocks p53-dependent apoptosis. U373MG cells were transfected with antisense oligonucleotides (AS) or sense oligonucleotides (SE) (1 µM) using Lipofectin reagent (GIBCO-BRL) for 4 hr, and then the cells were infected with various doses of Ad-p53. Forty-eight hours after infection, apoptotic cells were evaluated by FACS analysis.

The result indicated that FITC-labeled control oligonucleotides that were used for transfection using Lipofectin reagent were incorporated into the nucleus of greater than 90% of U373MG cells within 4 hr after transfection (data not shown). Pretreatment of U373MG cells with AS1 but not with SE1 significantly inhibited the induction of p53AIP1 expression (FIG. 13) as well as the induction of p53-induced apoptosis (FIG. 14). These results suggest that p53AIP1 is an important and essential factor for p53-dependent apoptosis.

EXAMPLE 7

Role of p53AIP1 in Mitochondrial Apoptotic Pathway

To determine whether p53AIP1 is a common mediator in a variety of apoptotic pathways, the present inventors examined its function using three different apoptosis-stimulators, staurosporine (STS) TNFα, and UV irradiation. TNFα stimulates apoptosis through the cell death-receptor pathway independent of the mitochondrial pathway (Li, K. et al., Cell 101: 389-399, 2000). UV irradiation and STS induce apoptosis by down-regulating mitochondrial membrane potential through the mitochondrial pathway, and then triggering release of cytochrome c (Matsuyama, S. et al., Nat. Cell Biol., 2: 318-325, 2000; Scarlett, J. L. et al., FEBS Lett., 475:267-272, 2000; Shimizu, S. et al., J. Cell Biol. 152: 237-250, 2001).

Cells were plated 24 hr before apoptosis-inducing treatment, and grown to 60%-70% confluency at the time of treatment. To test whether the expression of p53AIP1 in response to apoptotic stresses, MCF7 (breast carcinoma) cells were continuously incubated with staurosporine or TNFα, or were treated with UV at given dosages ($J/m^2$) using a UV cross-linker (Stratagene). Floating and adherent cells were collected, and subjected to analyses by Western blotting, FACS, and RT-PCR analysis. For FACS analysis, adherent and detached cells were combined and fixed with 75% ethanol at 4° C. After rinsed twice with PBS, cells were incubated at 37° C. for 30 min with 1 ml PBS containing boiled RNase. Cells were then stained in 1 ml PBS containing 10 μg of propidium iodide. The cells ($2\times10^4$ or more) were analyzed in a flow cytometer (FACScalibur; Becton Dickinson) to determine the percentage of sub-G1 nuclei in the cell population. In situ terminal transferase-mediated dUTP nick end-labeling (TUNEL) was performed using Apoptag Direct (Oncor) according to the manufacturer's instructions.

For RT-PCR analysis, total RNA was first isolated from cells using the RNeasy spin column kit (QIAGEN) according to the manufacturer's instructions. cDNAs were synthesized from 5 μg of total RNA using SuperScript Pre-amplification System (GIBCO-BRL). The exponential phase was determined for RT-PCR within 15 cycles to 30 cycles to allow semiquantitative comparisons among cDNAs derived from identical reactants. Each PCR was performed with initial denaturation at 94° C. for 2 min followed by 33 cycles (for p53AIP1), 24 cycles (for Noxa and PIG3), 25 cycles (for KILLER/DR5), 21 cycles (for Bax), or 18 cycles (for β2MG) of-94° C. for 30 sec, 55° C. to 59° C. for 30 sec, and 72° C. for 1 min, on a Gene Amp PCR system 9600 (Perkin Elmer).

```
Primer sequences were:
F (CCA AGT TCT CTG CTT TC/) and      SEQ ID NO:20

R (AGC TGA GCT CAA ATG CTG AC/)      SEQ ID NO:21 for p53AIP1;
F (GCA GCT CCT GGA TTC AAT TAC/) and SEQ ID NO:22

H (GCC TAT GTT CTT CTT CGC CTC/)     SEQ ID NO:23 for PIG3;
F (AGG ACT GTT CGT GTT CAG CTC/) and SEQ ID NO:24

R (GTG CAC CTC CTG AGA AAA CTC/)     SEQ ID NO:25 for Noxa;
F (CCA ACA GGT GTC AAC ATG TTG/) and SEQ ID NO:26

R (CAA TCT TCT GCT TGG CAA GTC/)     SEQ ID NO:27 for KILLER/DR5;
F (GGA GCT GCA GAG GAT GAT TG/) and  SEQ ID NO:28

R (CCA CAA AGA TGG TCA CGG TC/)      SEQ ID NO:29
``` and for Bax. PCR products were separated by electrophoresis on 2.5% agarose gels.

Incubation times and radiation doses were as follows: for RT-PCR, STS treatment was performed for 24 hr and TNFα and UV, for 48 hr; for Western blotting, STS, for 36 hr and TNFα and UV, for 48 hr; for FACS and TUNEL assays, STS (0.5 μM) and UV (50 $J/m^2$) for 36 hr and TNFα (10 ng/ml), for 72 hr; and for immunocytochemical analysis, STS (0.5 μM) and UV (50 $J/m^2$), for 24 hr and TNFα (10 ng/ml) for 48 hr.

Figure 15:
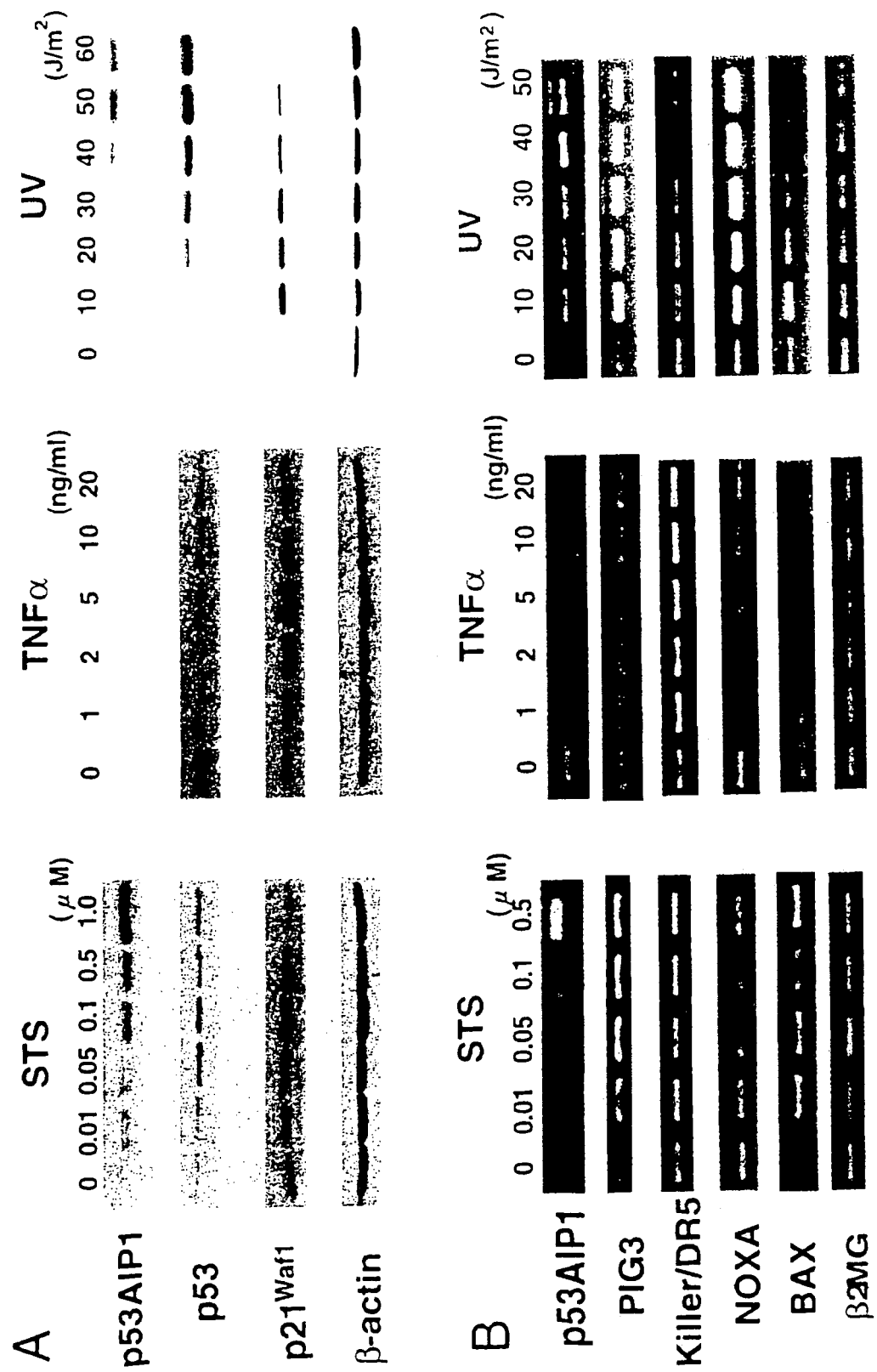
FIG. 15 presents photographs showing the expression of p53AIP1 through different apoptotic pathways, which was detected by Western blotting (A) and semiquantitative RT-PCR (B) analyses. MCF7 cells were collected at 36 hr after STS damage and 48 hr after UV or TNFα damage for Western blotting analysis, or 24 hr after STS damage, and 48 hr after UV or TNFα damage for RT-PCR. Expression of β-actin or β2MG serves as a control.
Figure 16:
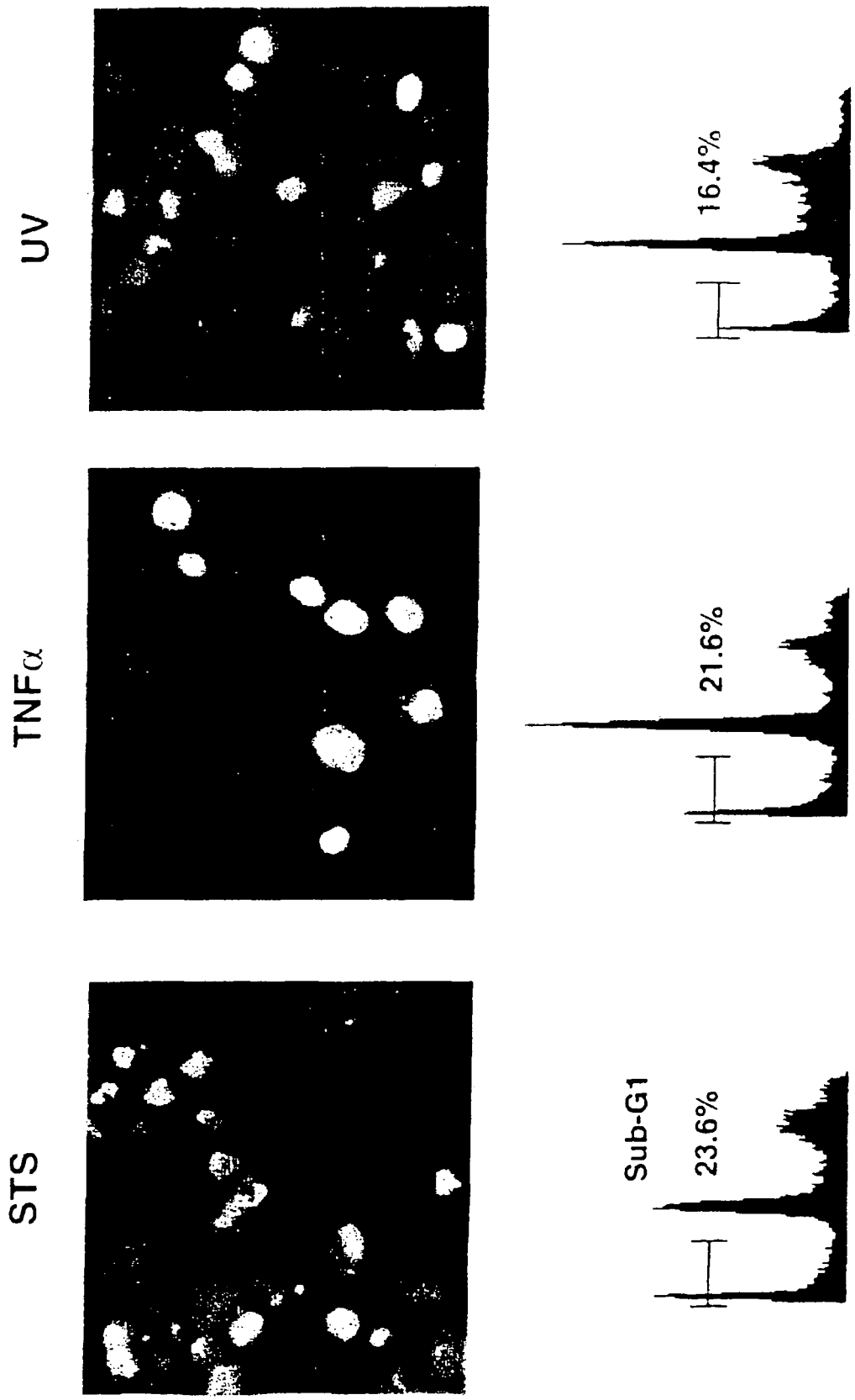
FIG. 16 presents photographs showing apoptotic cells (green or yellow signal) detected by TUNEL analysis, and diagrams showing the sub-$G_1$ fraction detected in FACS analysis. Apoptosis in MCF7 cells after continuous incubation with 0.5 µM STS for 36 hr or 10 ng/ml TNFα for 72 hr, or apoptosis in MCF7 cells 36 hr after UV irradiation at a dose of 50 J/m$^2$ was analyzed.

As shown in FIG. 15, the expression of p53AIP1 increased significantly in a dose-dependent manner during apoptotic induction by STS or UV irradiation but not by TNFα. Bax and PIG3 were also induced by damage with STS and UV irradiation, but their dose-dependent expressions were not observed in response to UV irradiation in contrast to the expression of p53AIP1. The expression level of Killer/DR5 mRNA was elevated during apoptotic induction by STS and TNFα, whereas Noxa was induced only when apoptosis was triggered by UV irradiation. In contrast, in lung carcinoma cells H1299 (p53−/−), none of the three apoptosis stimulators induced expression of p53AIP1. These results suggest that p53AIP1 is specifically associated with a mitochondrial apoptotic pathway in a p53-dependent manner (FIG. 16).

Figure 17:
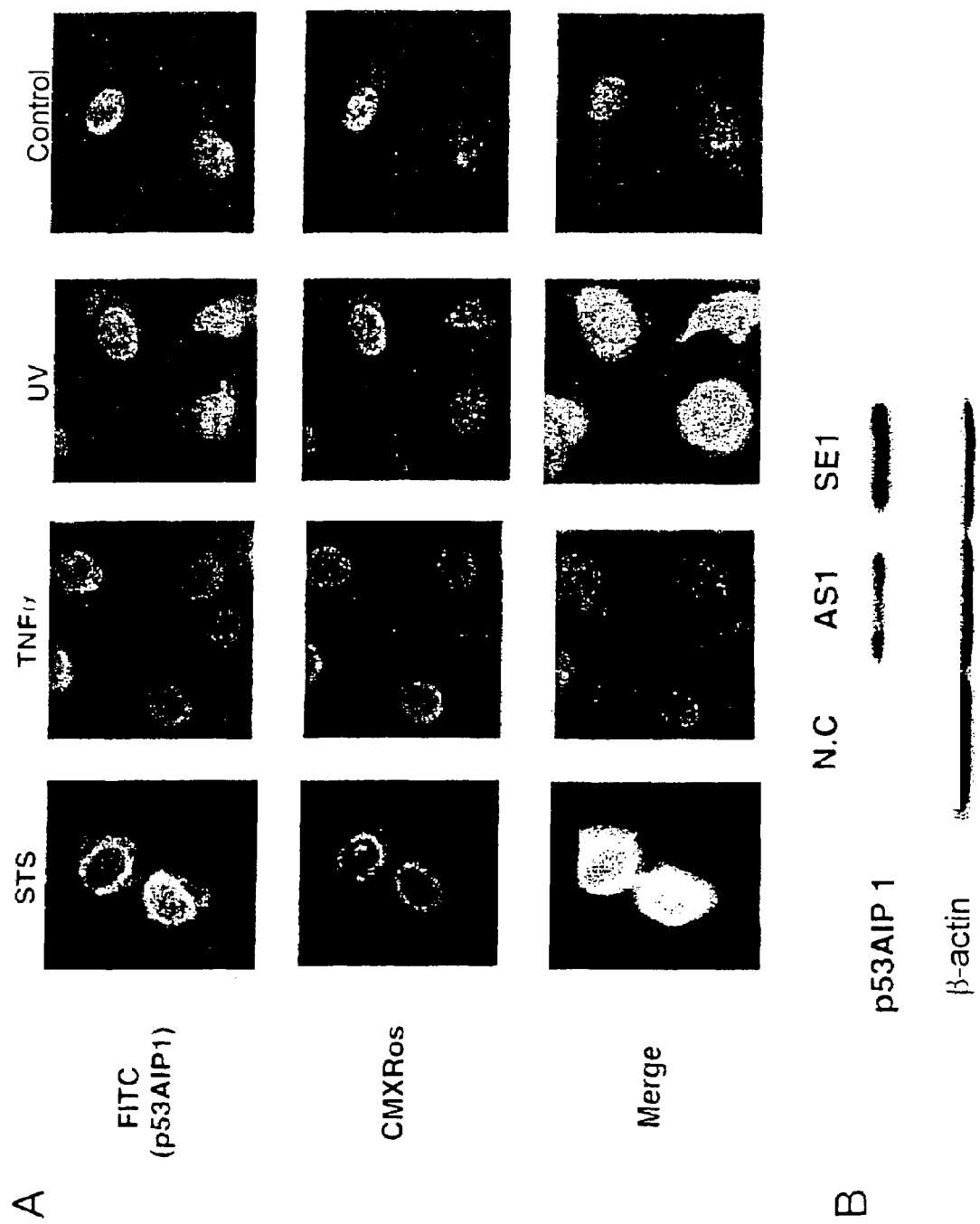
FIG. 17 presents photographs showing the expression of p53AIP1 protein in the mitochondria, and the function of p53AIP1 protein in apoptosis induced by UV or STS. A shows expression of p53AIP1 protein in the mitochondria of MCF7 cells damaged by UV irradiation (50 J/m$^2$), 0.5 µM STS, or 10 ng/ml TNFα. Twenty-four hours after STS and UV damage or 48 hr after TNFα damage, p53AIP1 protein and mitochondria in the cells were stained with FITC-conjugated rabbit anti-p53AIP1 antibody and Mito Tracker Red (CMXRos), respectively. The nuclei was visualized by DAPI staining. B shows inhibition of p53AIP1 expression by antisense oligonucleotide (AS). MCF7 cells were transfected with AS or sense oligonucleotides (SE) (1 µM) using Lipofectin reagent (GIBCO-BRL) for 4 hr, and then the cells were damaged by UV irradiation (50 J/m$^2$). Thirty-six hours after transfection, p53AIP1 expression was evaluated by Western blotting.

Next, the intracellular localization of endogenous p53AIP1 during apoptosis through different-pathways was identified. In human breast carcinoma cells MCF7 that were not exposed to any apoptosis stimulator, the expression of p53AIP1 was not detected. When the cells were treated with STS or UV irradiation, intense staining of p53AIP1 was observed in the mitochondria. No staining of p53AIP1 was observed after TNFα treatment (FIG. 17). To confirm the involvement of p53AIP1 in apoptotic processes, experiments using an antisense oligonucleotide (AS) corresponding to the p53AIP1 gene were performed. To inhibit endogenous p53AIP1 expression, antisense oligonucleotide (AS2: TCCCCTGGATGGGATC/SEQ ID NO: 30) and a control sense oligonucleotides (SE2: GATCCCATCCAGGGGA/SEQ ID NO: 31) were designed based on the sequence of the p53AIP1 gene, and then purified by HPLC. Cells were transfected with AS2 (1 μM) using tipofectin reagent (GIBCO-BRL) for 4 hr, and then treated with UV irradiation (50 J/m$^2$) or incubated with STS (0.5 μM) or TNFα (10 ng/ml). After 36 hr from the treatment, apoptotic cells were analyzed by FACS and TUNEL analysis.

Figure 18:
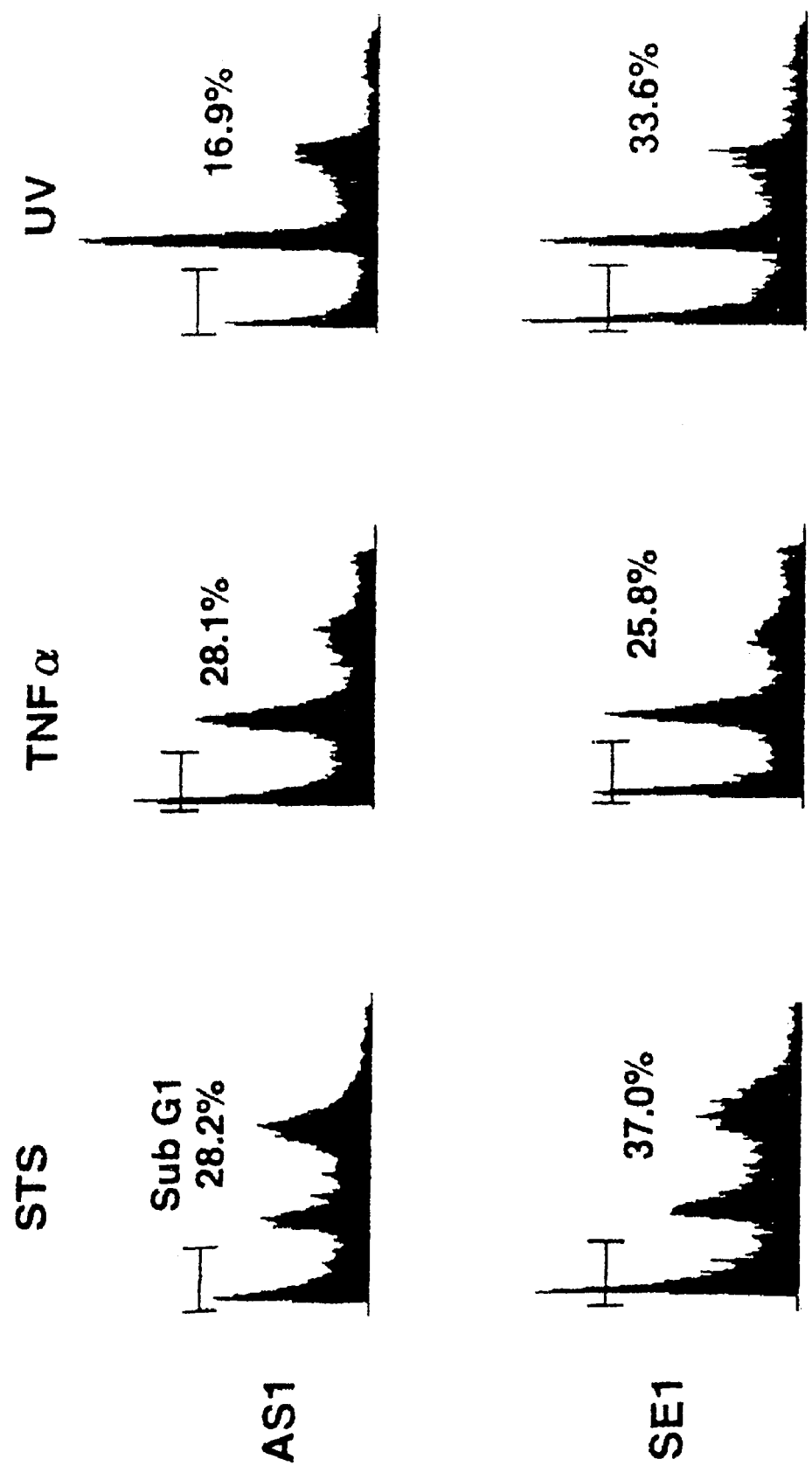
FIG. 18 shows the results of detection of STS, TNFα, and UV-dependent apoptosis by FACScan (the sub-$G_1$ fractions). MCF7 cells were transfected with AS or SE (1 µM) using Lipofectin reagent (GIBCO-BRL) for 4 hr, and treated with UV irradiation, STS or TNFα.

Pretreatment of MCF7 cells with AS caused a 50% reduction in the p53AIP1 expression level after UV irradiation, as compared with pretreatment with sense oligonucleotide (FIG. 17). Pretreatment with AS also caused the reduction of apoptotic (sub-G1) cell population from 37% to 28%, and from 33% to 16% after UV irradiation. However, AS treatment of MCF7 cells did not inhibit cell death induced by TNFα (FIG. 18).

EXAMPLE 8

Regulation by p53AIP1 of Mitochondrial ΔΨm and Release of Cytochrome c

Schuler et al. (Schuler, M. et al., J. Biol. Chem., 275: 7337-7342, 2000) reported that introduction of the p53 gene could induce down-regulation of mitochondrial membrane potential and promote release of cytochrome c. Other p53 downstream genes such as Noxa, PUMA, and Bax also enhance release of cytochrome c from mitochondria (Oda, E. et al., Science (Washington D.C.), 288: 1053-1058, 2000; Nakano, K. and Vousden, K. H., Mol. Cell, 7: 683-694, 2001; Jurgensmeier, J. M. et al., Proc. Natl. Acad. Sci. USA, 95: 4997-5002, 1998). To clarify the molecular mechanism of p53AIP1-inducible apoptosis, the present inventors examined the effect of overexpression of p53AIP1 on these phenomena.

Figure 19:
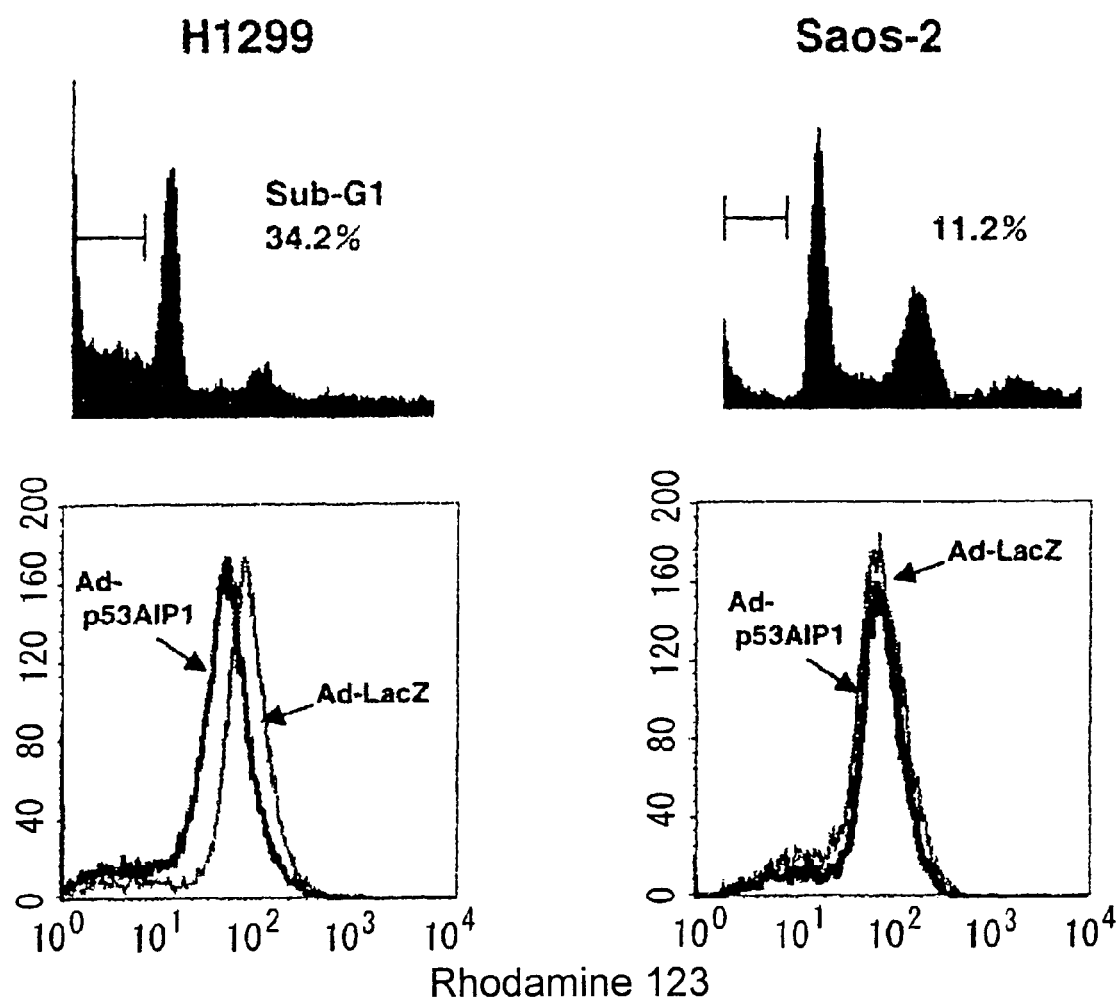
FIG. 19 shows the induction of apoptosis and down-regulation of mitochondrial ΔΨm by p53AIP1. H1299 and Saos-2 cells were infected with Ad-p53AIP1α or Ad-LacZ at an MOI of 100 pfu/cell. The mitochondrial ΔΨm (48 hr after infection) and the population of apoptotic cells (96 hr after infection) were analyzed by staining with Rhodamine 123 and by FACS analysis, respectively.

H1299 (lung carcinoma) and Saos-2 (osteosarcoma) cells were infected with Ad-p53AIP1α, and then the level of mitochondrial ΔΨm was estimated by staining with Rhodamine 123. Apoptosis was induced in H1299 cells by Ad-p53AIP1α, but Saos-2 cells were resistant to the effect of introduction of p53AIP1 gene. Down-regulation of mitochondrial ΔΨm was observed only in H1299 cells 48 hr after infection (FIG. 19). For investigation of the intracellular localization of cytochrome c, cell fractions were prepared at the times indicated in FIG. 20, and resulting cytosolic and mitochondrial fractions were subjected to Western blotting analysis with anti-cytochrome c antibody. The cell fractions were prepared as follows. First, cells were washed twice with PBS, and resulting cell pellets were suspended into 0.8 ml RS buffer (consisting of 10 mM NaCl, 1.5 mM MgCl$_2$, 10 mM Tris-HCl (pH 7.5)) and then homogenized by passing through a 21-gauge needle ten times. 11 ml of 2.5×MS Buffer (525 mM mannitol, 175 mM sucrose, 12.5 mM Tris-HCl (pH 7.5) and 2.5 mM EDTA (pH 7.5)) was added into the lysate and then centrifuged three times at 1,300×g for 5 min at 4° C. to remove nuclei and cell debris. Then, the supernatants were centrifuged at 17,000×g for 15 min at 4° C. to collect mitochondrial fractions. The remaining supernatants were further centrifuged at 100,000×g for 1 hr at 4° C. to obtain the final supernatants referred to as cytosolic fractions.

The result of the analysis indicated a remarkable translocation of cytochrome c from mitochondria to the cytosol 48 hr after infection of cells with Ad-p53AIP1α.

EXAMPLE 9

Interaction between p53AIP1 and bcl-2

Overexpression of bcl-2 can block the p53-dependent dissipation of mitochondrial ΔΨm and apoptosis (Wang, Y. et al., Oncogene, 8: 3427-3431, 1993; Chiou, S. K. et al., Mol. Cell Biol., 14: 2556-2563, 1994). Because p53AIP1 and bcl-2 are mitochondrial components associated with apoptosis, the present inventors speculated that the two proteins might influence the apoptotic process by interacting with each other. Expression vectors containing either HA-p53AIP1α or bcl-2 were cotransfected into COS7 cells. Antibodies against p53AIP1 were raised by immunizing rabbits with N-terminal and C-terminal peptides (Ab-1, and Ab-2, respectively) of p53AIP1, and further purified by the affinity chromatography using the antigens. Rabbit polyclonal anti-HA antibody (MBL, 561), mouse monoclonal anti-bcl-2 antibody (Santa Cruz, sc-509), mouse monoclonal anti-p21$^{WAF1}$ antibody (CALBIOCHEM, OP64), mouse monoclonal anti-p53 antibody (CALBIOCHEM, OP43), and mouse monoclonal anti-cytochrome c antibody (Santa Cruz, sc-7159) were also used. Immunoprecipitation was performed using (polyclonal) rabbit anti-HA antibody or (monoclonal) mouse anti-bcl-2 antibody, and protein G Sepharose beads. The precipitates were washed four times with lysis buffer (consisting of 0.5% NP-40, 150 mM NaCl, 20 mM Tris-HCl, 1 mM PMSF), and then eluted with Laemmli sample buffer (BIO RAD). Immunoblotting was performed as described previously (Oda, K. et al., Cell, 102: 849-862, 2000).

The result indicated that protein complexes containing p53AIP1α or bcl-2 were immunoprecipitated from cell extracts with rabbit polyclonal anti-HA antibody or mouse monoclonal anti-bcl-2 antibody, respectively. Western blotting analysis indicated that the immune complex precipitated with either antibody include both bcl-2 and HA-p53AIP1α proteins (FIG. 21A) Specific interaction between HA-p53AIP1β and bcl-2 was confirmed in the same manner.

Figure 21:
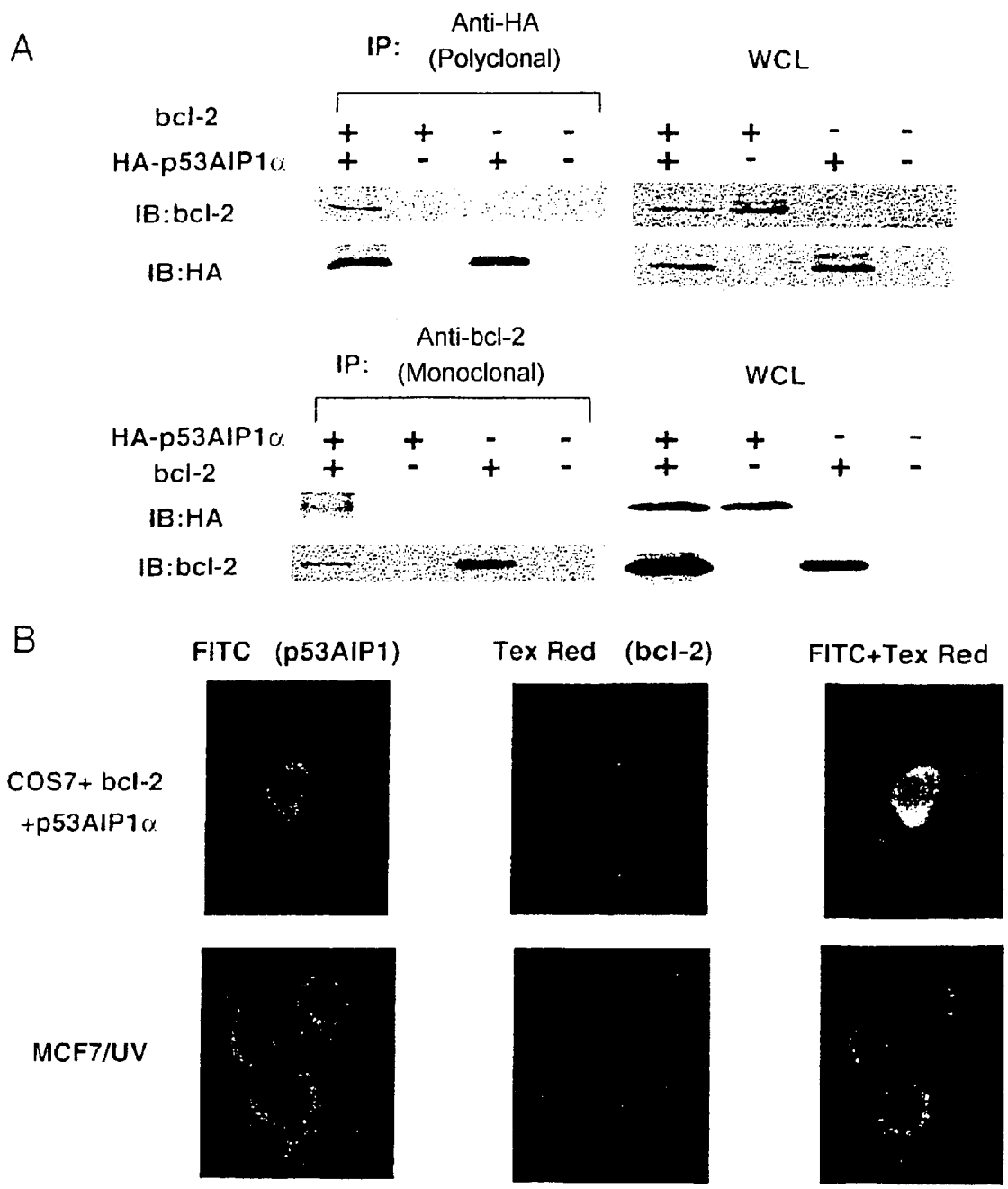
FIG. 21 presents photographs showing the physical interaction between p53AIP1 and bcl-2. A: COS7 cells were cotransfected with expression vectors for bcl-2 and HA-p53AIP1α, and cell extracts were isolated after 24 hr. A protein complex with bcl-2 or p53AIP1 was immunoprecipitated (IP) with anti-bcl-2 antibody or anti-HA antibody, and analyzed by immunoblotting (IB). WCL, whole cell lysate. B: Colocalization of bcl-2 and p53AIP1. Top panels: COS7 cells were cotransfected with expression vectors for bcl-2 and HA-p53AIP1α. After 24 hr, cells were double-stained with mouse monoclonal anti-bcl-2 antibody (red), and rabbit polyclonal anti-HA antibody (green) Both signals are overlapped in the double-color image as a yellow signal. Bottom panels: MCF7 cells were damaged by UV irradiation (50 J/m$^2$). After 36 hr, endogenous p53AIP1 (green), and bcl-2 (red) proteins were immunostained with rabbit polyclonal anti-p53AIP1 antibody, and mouse monoclonal anti-bcl-2 antibody, respectively.

Then, the intracellular locations of p53AIP1 and bcl-2 proteins were identified. Twenty-four hours after transfection of COS7 cells with expression vectors, cells were harvested and double-stained with mouse monoclonal anti-bcl-2 antibody and rabbit polyclonal anti-HA antibody. p53AIP1 (green), as well as bcl-2 (red) was stained in the cytoplasm as a granular pattern. The two signals were clearly overlapped in the double-color image resulting in a yellow signal (FIG. 21B, top). Both proteins. were confirmed to be localized in the mitochondria. MCF7 cells damaged by UV irradiation were also double-stained with rabbit polyclonal anti-human p53AIP1 antibody (Ab-2) and mouse monoclonal anti-human bcl-2 antibody for endogenous p53AIP1 and bcl-2, respectively. As shown at the bottom in FIG. 21B, endogenous p53AIP1 and bcl-2 proteins that were induced by damage were stained as the same pattern at the same location as those ectopically expressed.

EXAMPLE 10

Functional Interaction between p53AIP1 and bcl-2

Figure 20:
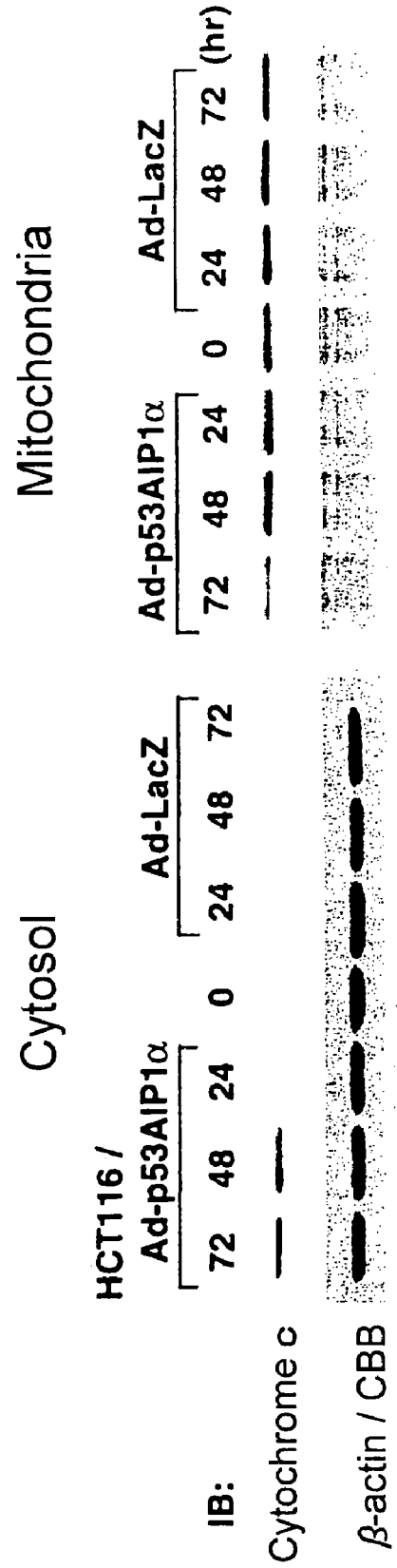
FIG. 20 is a photograph showing the release of cytochrome c by p53AIP1. Release of cytochrome c from mitochondria by overexpression of p53AIP1 is shown. HCT116 cells were infected with Ad-p53AIP1α or Ad-LacZ at MOI 100, and collected at the indicated time points. Cytosolic and mitochondrial fractions were subjected to immunoblotting.

As shown in FIGS. 19 and 20, the experiments by the present inventors clearly indicated that p53AIP1 itself regulated mitochondrial $\Delta\Psi m$ and triggered the release of cytochrome c. Bcl-2 is well known as an important regulator for mitochondrial $\Delta\Psi m$ that also blocks the release of cytochrome c from mitochondria. Based on these facts and the interaction between p53AIP1 and bcl-2 in mitochondria, the present inventors presumed that p53AIP1 itself might regulate mitochondrial $\Delta\Psi m$ by interacting with bcl-2 and then trigger the release of cytochrome c. To test this hypothesis, the present inventors examined whether bcl-2 could inhibit p53AIP1-induced apoptosis and the change in mitochondrial $\Delta\Psi m$. pcDNA3.1-bcl-2 was cotransfected with pCMV-puromycin at a ratio of 5:1 into HeLa cells with Fugene 6 Reagent (Roche). Transfected cells were selected by culturing in medium containing 1.25 µg/ml puromycin for 20 days, and then bcl-2 expression was evaluated by immunocytochemical analysis. and immunoblotting. Cells stably expressing bcl-2 were referred to as HeLa-bcl-2 cells. Two independent cell lines (HeLa-bcl-2 (1) and HeLa-bcl-2 (2)) that were expressing bcl-2 were established by the transfection of bcl-2 expression vector into HeLa cells.

Figure 22:
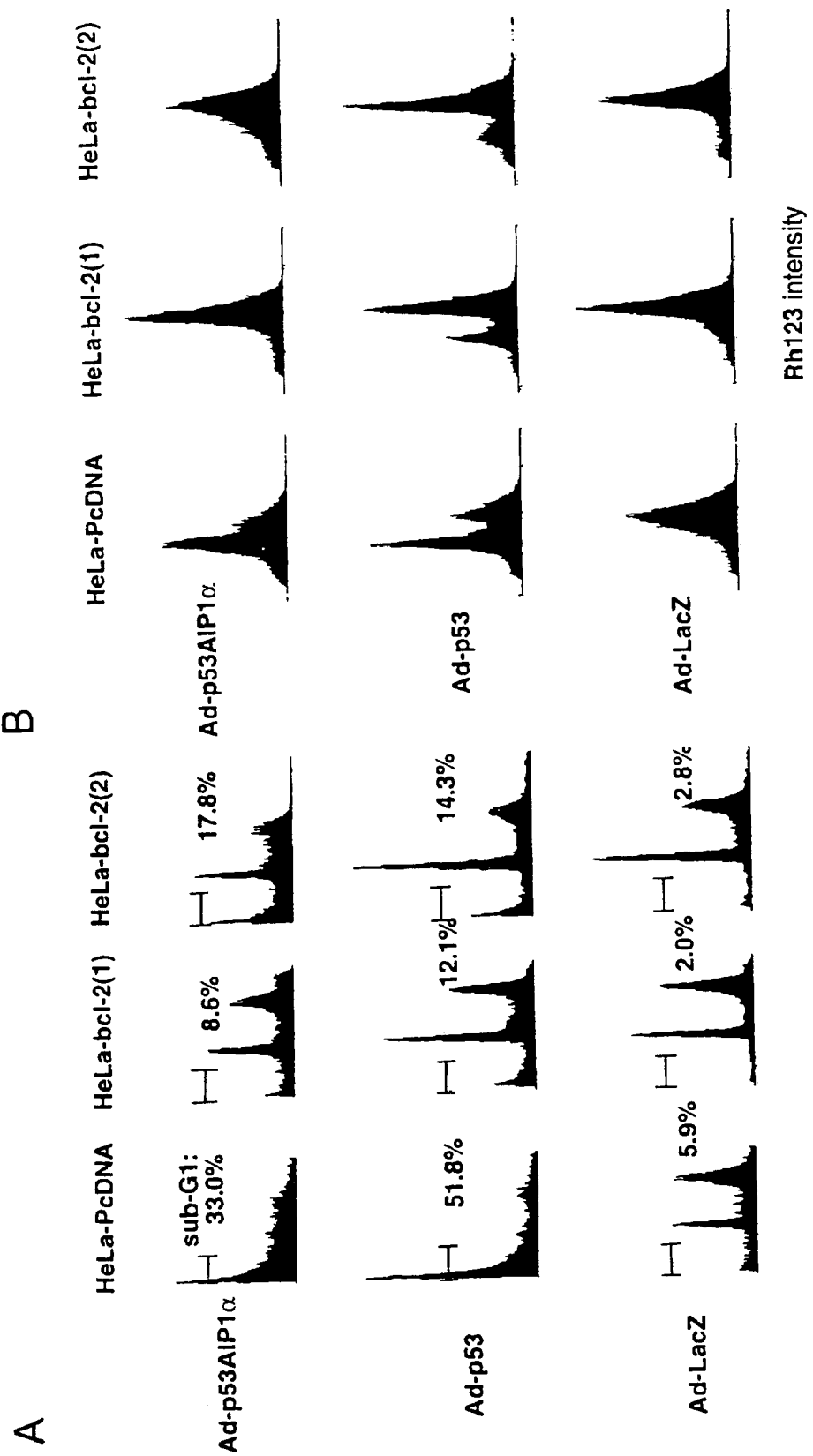
FIG. 22 shows the functional interaction between p53AIP1 and bcl-2 evaluated by FACS analysis. A: Inhibition by bcl-2 of apoptosis induced by Ad-p53 or Ad-p53AIP1α. Ad-p53AIP1α, Ad-p53, and Ad-LacZ were infected into three different cell lines, HeLa-pcDNA, HeLa-bcl-2 (1), and HeLa-bcl-2 (2), and apoptosis (sub-$G_1$ fraction) thus caused was evaluated by FACS analysis at 72 hr after infection. B: Down-regulation of mitochondrial ΔΨm by Ad-p53AIP1α and Ad-p53. Ad-p53AIP1α, Ad-p53, and Ad-LacZ were used to infect HeLa-pcDNA, HeLa-bcl-2 (1), and HeLa-bcl-2 (2) cell lines. The cells were labeled with Rhodamine 123 at 60 hr after infection, and fluorescence was analyzed by FACScan. The horizontal axis indicates $10^0$ at left end, $10^4$ at right end, and $10^2$ at center, respectively.

As shown in FIG. 22A, apoptosis could be induced in HeLa mock parental cells (transfected with the control vector pcDNA3.1 only) by infection with Ad-p53AIP1α or Ad-p53 but not with Ad-LacZ. In contrast, when two HeLa cell lines overexpressing bcl-2 were infected with Ad-p53AIP1α or Ad-p53, the number of apoptotic cells decreased significantly, suggesting that bcl-2 was able to block the apoptotic pathway that involves p53AIP1 and p53.

Next, the mitochondrial $\Delta\Psi m$ itself was analyzed. Detection of mitochondrial membrane potential was performed as follows. Cells were plated at the density of $5\times10^5$ cells/6-cm dish and infected 24 hr later with Ad-p53AIP1α, Ad-p53, or Ad-LacZ at MOI 100 pfu/cell. Sixty hours after infection, adherent and floating cells were collected by trypisinization, and washed twice with cold PBS. Rhodamine 123 (10 nM) in PBS was added to the cells, and were incubated for 30 min at 37° C. Fluorescence was measured by flow cytometry.

Induction of exogenous p53AIP1α and p53 proteins downregulated mitochondrial $\Delta\Psi m$ in HeLa mock parental cells, but induction of exogenous LacZ did not. However, this phenomenon was blocked in both of the HeLa cell lines overexpressing bcl-2 (FIG. 22B). The result indicates that bcl-2 can block the down-regulation of mitochondrial $\Delta\Psi m$ induced by either p53AIP1α or p53, supporting the possibility that interaction between bcl-2 and p53AIP1 may regulate mitochondrial $\Delta\Psi m$ by balancing positive and negative effects.

EXAMPLE 11

Figure 23:
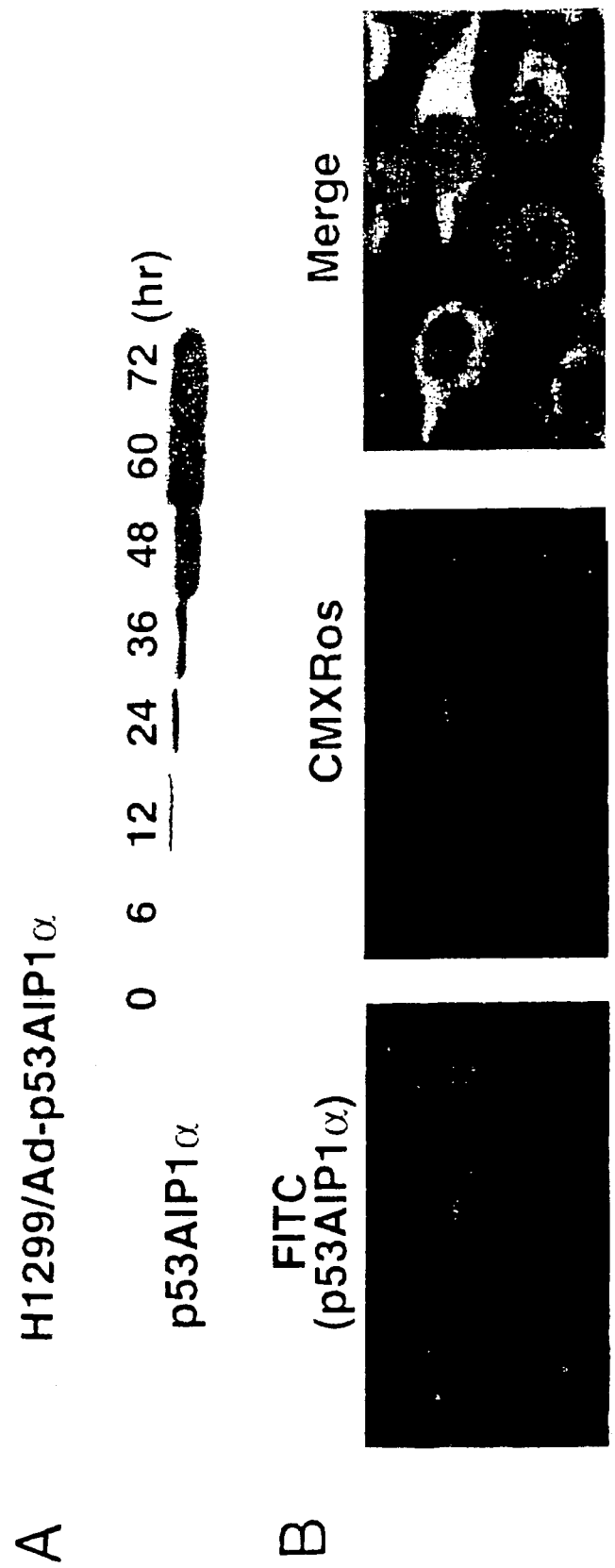
FIG. 23 presents photographs showing expression of exogenous p53AIP1 protein in H1299 cells infected by adenovirus vectors. A: Expression of exogenous p53AIP1α in lung carcinoma cells infected with Ad-p53AIP1α. H1299 cells were collected at the indicated time points after infection, and cell lysates were subjected to immunoblotting with anti-p53AIP1 antibody. B: p53AIP1α (green) and mitochondria (red) which were stained with anti-p53AIP1 antibody, and anti-mitochondria antibody, respectively. The double-color image indicates that p53AIP1 signal (green) is overlapped with that of mitochondria at 24 hr after infection.
Figure 24:
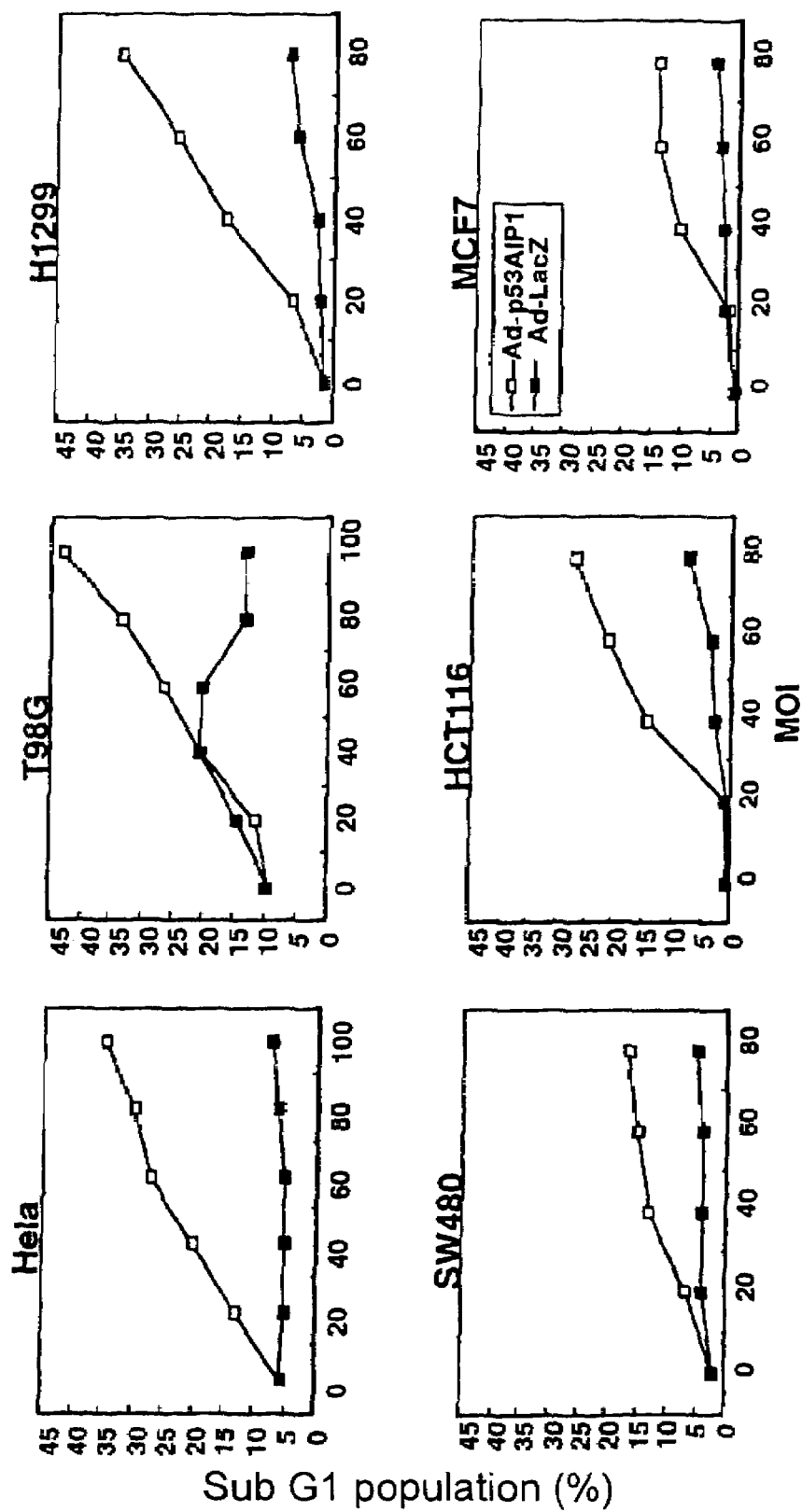
FIG. 24 shows anti-tumor effect of p53AIP1 on various cancer cell lines in vitro. Apoptosis was induced in six cancer cell lines by infection with various doses (MOI) of Ad-p53AIP1α. Apoptotic cells were analyzed by FACScan at 96 hr after infection.
Figure 25:
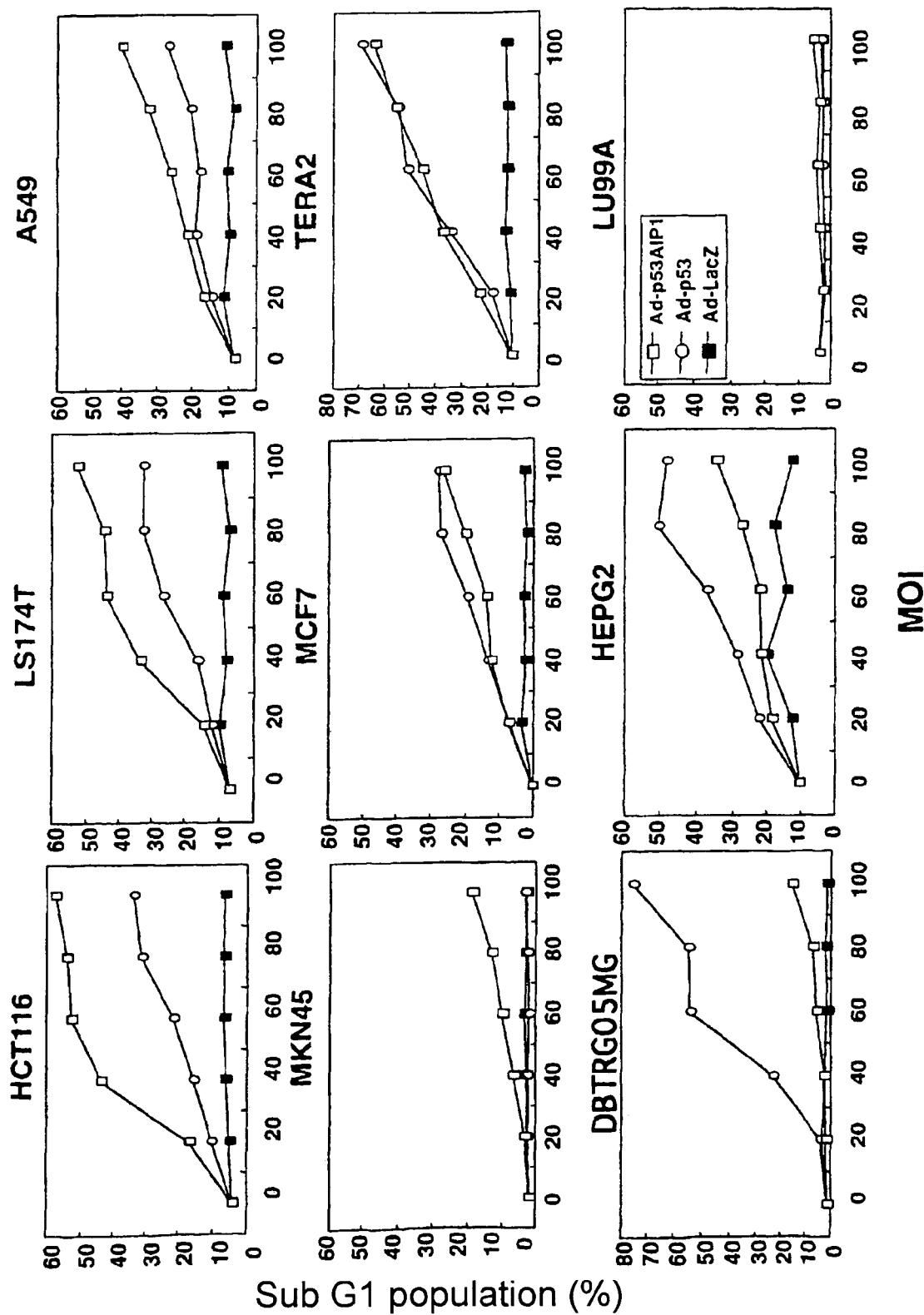
FIG. 25 shows the result of FACS analysis for apoptosis induced in six cancer cell lines (p53 wild-type) by infection with various doses (MOI) of Ad-p53 or Ad-p53AIP1α. Apoptotic cells were analyzed by FACScan at 96 hr after infection.

Anti-tumor Effect of p53AIP1 in Various Tumor Cell Lines in vitro p53AIP1 was expressed significantly in a time-dependent manner in the mitochondria of H1299 cells after infection with Ad-p53AIP1α (FIGS. 23A and B). To evaluate the ability of p53AIP1 to induce apoptosis in cancer cells derived from avariety of tissues, six different cancer cell lines were infected with Ad-p53AIP1α: HeLa in which p53 is inactivated by EIA; T98G (p53 mutant); H1299 (p53 null); SW480 (p53 mutant); HCT116 (p53 wild-type); and MCF7 (p53 wild-type). Infection with Ad-p53AIP1α significantly induced apoptosis in all the six cell lines regardless of their p53 status, although the extent of apoptosis varied from one cell line to another (FIG. 24). Cancer cells containing wild-type p53 protein are relatively resistant to p53 gene therapy (Gomez-Manzano, C. et al., Cancer Res., 56: 694-699, 1996; Harris M. P. et al., Cancer Gene Ther. 3: 121-130 (1996)). Thus, the present inventors compared the in vitro anti-tumor effect of the p53AIP1 gene with that of the p53 gene on nine cancer cell lines containing wild-type p53 (WTp53): HCT116 (colon cancer), LS174T (colon cancer), A549 (lung cancer), MKN45 (gastric cancer), MCF7 (breast cancer), TERA2 (teratoma), DBTRG05MG (glioma), HepG2 (Hepatocarcinoma), and Lu99A (lung cancer). All the nine cell lines revealed 100% infection with Ad-7LacZ vector. Ectopic expression of exogenous p53AIP1 by adenovirus-mediated gene transfer effectively induced apoptosis in six of the WTp53 cancer cell lines (FIG. 25). In fact, four of the six cell lines were killed more effectively by p53AIP1 than by p53.

Industrial Applicability

The present invention provides a novel target gene, referred to as "p53AIP1", for p53 tumor suppressor protein. The gene functions closely related to p53-mediated apoptosis. T98G cells transfected with p53AIP1 expression vector or infection with an adenovirus vector comprising p53AIP1 induces a massive apoptotic cell-death. Therefore, apoptosis-mediated therapy for human cancers would be possible by introduction of p53AIP1 gene of the present invention using the expression vector or adenovirus vector. Since the p53AIP1 gene of the present invention and a protein encoded by the gene are useful for development of therapeutic agents for apoptosis-associated diseases, as a target molecule for such diseases.

Moreover, the present inventors found that p53AIP1 effectively induces apoptosis in both p53-susceptible and p53-resistant cancer cell lines. Thus, it is indicated that p53AIP1 is a direct mediator for p53-dependent apoptosis pathway in the mitochondria. Therefore, the p53AIP1 gene of the present invention may be utilized for cancer therapies more broadly than p53 itself. The adenovirus vector comprising p53AIP1 is expected as a promising drug for gene therapy targeted at cell death of cancer cells, in particular, p53 resistant cells containing wild-type p53.

Furthermore, the present invention provides a method of screening for a candidate compound that can regulate induction of apoptosis. Use of this method is expected to develop preventive agents as well as therapeutic agents, which comprise the compound as an effective component, for both cancers and apoptosis-associated diseases.

SEQUENCE LISTING

<160> NUMBER OF SEQ ID NOS: 31

<210> SEQ ID NO 1
<211> LENGTH: 806
<212> TYPE: DNA
<213> ORGANISM: Homo sapiens
<220> FEATURE:
<221> NAME/KEY: CDS
<222> LOCATION: (211)..(582)

<400> SEQUENCE: 1

```
ccctgagagg ccgtgctcgg gctcgcctgc tcagctcact ccgaaagcct ctgctcagac      60
ctgcacccag tcacagcagc acagatgtgc aggaggagac catttccacg gaccctccga     120
ctcctaggag gcagtcccct agggactggc cctaacaaca aatgaggaga agccaagttc     180
tctgctttct gcagacaggg cctcccctgg atg gga tct tcc tct gag gcg agc     234
                                  Met Gly Ser Ser Ser Glu Ala Ser
                                   1               5 ttc aga tct gct caa gct tcc tgc agt ggg gcc agg agg cag ggc ctg      282
Phe Arg Ser Ala Gln Ala Ser Cys Ser Gly Ala Arg Arg Gln Gly Leu
         10                  15                  20 ggc agg gga gac cag aac ctc tcg gtg atg cct ccg aat ggc agg gct      330
Gly Arg Gly Asp Gln Asn Leu Ser Val Met Pro Pro Asn Gly Arg Ala
     25                  30                  35                  40 cag aca cac aca cct ggc tgg gtt tca gat ccc tta gtt ttg ggt gcc      378
Gln Thr His Thr Pro Gly Trp Val Ser Asp Pro Leu Val Leu Gly Ala
                 45                  50                  55 caa gtt cac gga ggg tgc cgg gga ata gaa gct ctg tca gtc tcg tct      426
Gln Val His Gly Gly Cys Arg Gly Ile Glu Ala Leu Ser Val Ser Ser
             60                  65                  70 gga tct tgg tcc tca gca act gtc tgg atc ctg aca ggc ctt ggt cta      474
Gly Ser Trp Ser Ser Ala Thr Val Trp Ile Leu Thr Gly Leu Gly Leu
         75                  80                  85 ggt ctc tcc agg cct ttc ctt cct gga gcc aca gtg ctt aga gac agg      522
Gly Leu Ser Arg Pro Phe Leu Pro Gly Ala Thr Val Leu Arg Asp Arg
     90                  95                 100 cca ctg ggg tca gca ttt gag ctc agc tat gat cag aaa aaa gca ccg      570
Pro Leu Gly Ser Ala Phe Glu Leu Ser Tyr Asp Gln Lys Lys Ala Pro
105                 110                 115                 120 ttg agg ttg cag tgagccgaga tcacgccact gcactccagc ctgggcgaca          622
Leu Arg Leu Gln gagagagact ccatctcaaa acaaaaacaa acaaacaaac agaaagcacc gtcgagaaat    682
ggctccagcg ctgactagcg gccacctcat ttcccccctt gaccactggg ccagttgggt    742
ggctaggttg cctcattttg catccttctg tatccccaaa tctgaaataa agctggaaa    802 aaaa                                                                806
```

<210> SEQ ID NO 2
<211> LENGTH: 124
<212> TYPE: PRT
<213> ORGANISM: Homo sapiens

<400> SEQUENCE: 2

```
Met Gly Ser Ser Ser Glu Ala Ser Phe Arg Ser Ala Gln Ala Ser Cys
 1               5                  10                  15

Ser Gly Ala Arg Arg Gln Gly Leu Gly Arg Gly Asp Gln Asn Leu Ser
             20                  25                  30

Val Met Pro Pro Asn Gly Arg Ala Gln Thr His Thr Pro Gly Trp Val
```

```
                35                  40                  45
Ser Asp Pro Leu Val Leu Gly Ala Gln Val His Gly Gly Cys Arg Gly
    50                  55                  60
Ile Glu Ala Leu Ser Val Ser Ser Gly Ser Trp Ser Ser Ala Thr Val
 65                  70                  75                  80
Trp Ile Leu Thr Gly Leu Gly Leu Gly Leu Ser Arg Pro Phe Leu Pro
                 85                  90                  95
Gly Ala Thr Val Leu Arg Asp Arg Pro Leu Gly Ser Ala Phe Glu Leu
            100                 105                 110
Ser Tyr Asp Gln Lys Lys Ala Pro Leu Arg Leu Gln
        115                 120

<210> SEQ ID NO 3
<211> LENGTH: 777
<212> TYPE: DNA
<213> ORGANISM: Homo sapiens
<220> FEATURE:
<221> NAME/KEY: CDS
<222> LOCATION: (211)..(468)

<400> SEQUENCE: 3
ccctgagagg ccgtgctcgg gctcgcctgc tcagctcact ccgaaagcct ctgctcagac      60
ctgcacccag tcacagcagc acagatgtgc aggaggagac catttccacg gaccctccga    120
ctcctaggag gcagtccctt agggactggc ctaacaaca aatgaggaga agccaagttc     180
tctgctttct gcagacaggg cctcccctgg atg gga tct tcc tct gag gcg agc    234
                                  Met Gly Ser Ser Ser Glu Ala Ser
                                    1               5 ttc aga tct gct caa gct tcc tgc agt ggg gcc agg agg cag ggc ctg    282
Phe Arg Ser Ala Gln Ala Ser Cys Ser Gly Ala Arg Arg Gln Gly Leu
     10                  15                  20 ggc agg gga gac cag aac ctc tcg gtg atg cct ccg aat ggc agg gct    330
Gly Arg Gly Asp Gln Asn Leu Ser Val Met Pro Pro Asn Gly Arg Ala
 25                  30                  35                  40 cag aca cac aca cct ggc tgg gtt tca gat ccc tta gtt ttg ggt gcc    378
Gln Thr His Thr Pro Gly Trp Val Ser Asp Pro Leu Val Leu Gly Ala
             45                  50                  55 caa gtt cac gga ggg tgc cgg gga ata gaa gct ctg tca gtc tcg tct    426
Gln Val His Gly Gly Cys Arg Gly Ile Glu Ala Leu Ser Val Ser Ser
         60                  65                  70 gga tct tgg tcc tca gca act gtc tgg atc ctg aca gtg cag              468
Gly Ser Trp Ser Ser Ala Thr Val Trp Ile Leu Thr Val Gln
     75                  80                  85 taagagcttg cctggcctgt gtgcagagct gcctcatcct gaaattctgg gagttgaaag    528
ccccagggca acccttaacc aatgggggaa aagcattggt gtgtaaatcc cccagcttcc    588
ctgggtgggc tgcagctgag ccatattcta catgacactt ccgaggatcc ccagtgggca    648
tgacctcaat cgcccacatt ggatgccaca acctgcactg ctttttctcc cttccctgtg    708
ggtctctctc tgcacttcct cccttgtgca ttctaggttc accttccaaa taaatgatgt    768
gcactcagg                                                            777

<210> SEQ ID NO 4
<211> LENGTH: 86
<212> TYPE: PRT
<213> ORGANISM: Homo sapiens

<400> SEQUENCE: 4

Met Gly Ser Ser Ser Glu Ala Ser Phe Arg Ser Ala Gln Ala Ser Cys
```

```
                    1               5              10              15
               Ser Gly Ala Arg Arg Gln Gly Leu Gly Arg Gly Asp Gln Asn Leu Ser
                             20                  25                  30

Val Met Pro Pro Asn Gly Arg Ala Gln Thr His Thr Pro Gly Trp Val
                         35                  40                  45

Ser Asp Pro Leu Val Leu Gly Ala Gln Val His Gly Gly Cys Arg Gly
                     50                  55                  60

Ile Glu Ala Leu Ser Val Ser Ser Gly Ser Trp Ser Ala Thr Val
               65                  70                  75                  80

Trp Ile Leu Thr Val Gln
                               85

<210> SEQ ID NO 5
<211> LENGTH: 2659
<212> TYPE: DNA
<213> ORGANISM: Homo sapiens
<220> FEATURE:
<221> NAME/KEY: CDS
<222> LOCATION: (211)..(534)

<400> SEQUENCE: 5
ccctgagagg ccgtgctcgg gctcgcctgc tcagctcact ccgaaagcct ctgctcagac    60
ctgcacccag tcacagcagc acagatgtgc aggaggagac catttccacg accctccga    120 ctcctaggag gcagtccctt agggactggc cctaacaaca aatgaggaga agccaagttc    180
tctgctttct gcagacaggg cctcccctgg atg gga tct tcc tct gag gcg agc    234
                                 Met Gly Ser Ser Ser Glu Ala Ser
                                  1               5 ttc aga tct gct caa gct tcc tgc agt ggg gcc agg agg cag ggc ctg    282
Phe Arg Ser Ala Gln Ala Ser Cys Ser Gly Ala Arg Arg Gln Gly Leu
            10                  15                  20 ggc agg gga gac cag aac ctc tcg gtg atg cct ccg aat ggc agg gct    330
Gly Arg Gly Asp Gln Asn Leu Ser Val Met Pro Pro Asn Gly Arg Ala
         25                  30                  35                  40 cag aca cac aca cct ggc tgg gta agt ccc tgc agt gaa aac cga gac    378
Gln Thr His Thr Pro Gly Trp Val Ser Pro Cys Ser Glu Asn Arg Asp
                 45                  50                  55 ggt ctt ttg cct gcc aca gcc ccg ggc aga ctc tgc tct cac cgt ggt    426
Gly Leu Leu Pro Ala Thr Ala Pro Gly Arg Leu Cys Ser His Arg Gly
             60                  65                  70 gcc gac atc cca agt ttt cag act cac cag gac cca gtg aca gca tct    474
Ala Asp Ile Pro Ser Phe Gln Thr His Gln Asp Pro Val Thr Ala Ser
        75                  80                  85 ggg tcc tca gag ctg cat gcg gac tgt ccc cag ttc aga gca ttg gac    522
Gly Ser Ser Glu Leu His Ala Asp Cys Pro Gln Phe Arg Ala Leu Asp
    90                  95                 100 aga gct ggg aac tgacagccct gatcaatagt cccaagagga aggccagccc        574
Arg Ala Gly Asn
105 tcctcctcct cggaatcctg ggtttctagg aggcagaaag gttttctgag aaacaaggct    634 tttggaagga aggtggtgcc tggctgcatc cagaaagtga gagctaaatg gagaggctga    694 acaaaggacg catgtggagc gcatgggagg gaaggctggg gtgcagggc tccgggcctg    754 ctcttctgcg tccaccccgg atcctgcttt tgtccagatg ggcctcggag caccagtcac    814 ttactccaag aagtcgtttc ctgtggccaa taatgaagat gacgcactcg gaagcttgtg    874 ggctctgagg agggggtaag gatgcagggg ccatgcattc atcccagcac aggcagcgca    934 tggctccgga agcagacaca ggccaggcct gggccaggag tctgccagga gccaggagcg    994
```

```
cctacacctc cctggaggcc cacacttctc tccccagaag ctcacacgca gcgtctgagg   1054
tgcagggccc aggtgtgctg gggtgacaaa gccccgagct gtggtgatgg gagggaggaa   1114
gcgccggttt atgtctgttc tttgggctga tttgctgtct ctgtctttgt ctctaatgtc   1174
ctttgcacca ctgaccttga ggagcctttt gttcctcctg tcccagtttg gtttccatgg   1234
gaacctgagt ggcagcgtca tcactttgct gaggtgaaat gccctggat gccatgaata    1294 cctaggggaa aacctgccag agaagaataa accatccaag agacggcgct gcagggcctc   1354
acagtctgct tccatttcct ctcaggtttc agatccctta gttttgggtg cccaagttca   1414
cggagggtgc cggggaatag aagctctgtc agtctcgtct ggatcttggt cctcagcaac   1474
tgtctggatc ctgacaggtg tgtgataatt acttagtgaa ttcatgggtg tgggccgtga   1534
tagaattaag tgatttgatg tcctctcgat aaatccaggt aacgacatag ggttttttga   1594
gtttgaccct ctcctgaaat ttgccatctg acaaaatgac atcatggcag agttgtaaac   1654
tgctgtggat gtatttttatt taatttctca aattaaaata aaaggtaacg gtacacttaa   1714
gagtggtcac tacagccaag ctaattgaca cccactgaac tttctggaat gggccatagg   1774
atgctggaca ataggacaga tttggaatga gcagtcttcc attccaactt tagtttctgc   1834
aaagctgttg agagcatgga gccaggctgc ggggtctggg ttcaaatcct gactctacca   1894
cttaggagct gtgtgtacat gggcaggaca actggcctgc ctgagtctca gtgtaggtgt   1954
ctgtaaaatg gaatgataat agcttccatc tcacagattc actgtgtggg taaaatgata   2014
gatatgaaat gctaagaaca gcacctgtac gtagtatgtc ctacatatct tactgttatc   2074
attagcatat tttgtttatt ccaagataca ttttttttgg cccatttgat atctatgaaa   2134
tctaaagatt ttttttcctg tcttgggaga tagaataatg atgtgcctta caatggattg   2194
tgttttagat tcactgaaat tcattattgt tgttttatc cctggtctgt aacatgatat    2254
ttggtaaata acaaggactc catacgtttt gcaaagagta aattctctcc ctccctactg   2314
aggccttggt ctaggtctct ccaggccttt ccttcctgga ccacagtgc ttagagacag    2374 gccactgggg tcagcatttg agctcagcta tgatcagaaa aaagcaccgt tgaggttgca   2434
gtgagccgag atcacgccac tgcactccag cctgggcgac agagagagac tccatctcaa   2494
aacaaaaaca aacaaacaaa cagaaagcac cgtcagaaa tggctccagc gctgactagc    2554
ggccacctca tttcccccct tgaccactgg gccagttggg tggctaggtt gcctcatttt   2614
gcatccttct gtatccccaa atctgaaata aagctggaa aaaaa                    2659
```

<210> SEQ ID NO 6
<211> LENGTH: 108
<212> TYPE: PRT
<213> ORGANISM: Homo sapiens

<400> SEQUENCE: 6

```
Met Gly Ser Ser Ser Glu Ala Ser Phe Arg Ser Ala Gln Ala Ser Cys
  1               5                  10                  15

Ser Gly Ala Arg Arg Gln Gly Leu Gly Arg Gly Asp Gln Asn Leu Ser
             20                  25                  30

Val Met Pro Pro Asn Gly Arg Ala Gln Thr His Thr Pro Gly Trp Val
         35                  40                  45

Ser Pro Cys Ser Glu Asn Arg Asp Gly Leu Leu Pro Ala Thr Ala Pro
     50                  55                  60

Gly Arg Leu Cys Ser His Arg Gly Ala Asp Ile Pro Ser Phe Gln Thr
 65                  70                  75                  80
```

His Gln Asp Pro Val Thr Ala Ser Gly Ser Ser Glu Leu His Ala Asp
            85                  90                  95
Cys Pro Gln Phe Arg Ala Leu Asp Arg Ala Gly Asn
            100                 105

<210> SEQ ID NO 7
<211> LENGTH: 9305
<212> TYPE: DNA
<213> ORGANISM: Homo sapiens

<400> SEQUENCE: 7

| | | | | | |
|---|---|---|---|---|---|
| tccaaaatag | aagcagcttt | tgaggaattt | ggagggataa | acggaatag | tatgtctgaa | 60 |
| agttggcaac | atgtaaaaag | gctaaaaatg | acaattctgc | ctgtgatact | atgtctagtg | 120 |
| tgcaacgctt | cattcaaaag | gcaggcacgt | ctccctcca | ggcgggagtg | ggaatctcag | 180 |
| tggggaaccg | ggaactgcgt | ttgagctgat | gcagactcag | ggtcaactcg | acaagggagc | 240 |
| ccggcaccca | gacacagcgg | cgttcacctc | accttgcacc | gtctttgtcg | gtcttacagg | 300 |
| catcagcttt | cccagcctca | tttgagccgg | gatctgagtt | gcatttcttt | ctgggtcagg | 360 |
| ccttgccatt | agggagagat | gaagtcaact | gatgagcgtg | ccagccttga | ggaaggacag | 420 |
| agtgcgggaa | gcagagtgtg | ggaagttgga | aaaataatc | tgcaaggtaa | acaccttcaa | 480 |
| gtcaatttca | agaggctggc | tagaaaccgc | caggacttca | gggggccctg | tctcgcgggt | 540 |
| ctccctgcgc | cctcagcact | ttggcttggt | ataaggccac | cttgtccctg | aagagaggcc | 600 |
| tattttaagc | tgagcaagaa | aaggtgagaa | agactaaaat | cagctttgtg | cagagacgcc | 660 |
| aatttctgct | gcacacatgg | aaacgatgtg | cacatacagc | aagctggccc | agctcccggc | 720 |
| cacgtggctc | acactgtccg | tgctcaccca | cccgttgcct | tcaccccag | cagcactggt | 780 |
| tgtgaaaagg | gtaactgcct | gagccacccc | accactgcgg | gcctgccaag | gacaggcagg | 840 |
| aactcagcca | tgccccgcaa | ggagcccagg | ggcatctcca | gggacggctc | cccagcctat | 900 |
| gggctcgctc | cctgagaggc | cgtgctcggg | ctcgcctgct | cagctcactc | cgaaagcctc | 960 |
| tgctcagacc | tgcacccagt | cacagcagca | cagatgtgca | ggaggagacc | atttccacgg | 1020 |
| accctccgac | tcctaggagg | caggtgagga | gaggggagg | gaggggacca | gcgctggtgc | 1080 |
| ttcaggtatg | ctctggccac | tgcgattcac | tctgcttttgt | gcttgggtt | tcacacgcat | 1140 |
| ctcggtgact | gtgtgcggaa | ggtacagtcg | tgaccatgcg | caggtgaggc | ctggaggagg | 1200 |
| tcagctaaac | tgctctctct | caatggttct | gaaccctgag | agtacatcag | agtcacctgg | 1260 |
| aggacttacg | aaaacacaca | ctgcagaatt | tctgacttgg | tcgatgcagg | ttggggccaa | 1320 |
| aaatgtgtat | ctctaacagg | ttcctgggcg | atgctgacgc | cgatgctgtg | cgtcctgagc | 1380 |
| cacacttggg | gagctactgc | gcaagctcgc | acagctagcc | gaccgctgag | ctggggctca | 1440 |
| gacctgggtc | agtcctggtc | cacaggccag | cccctttctc | acgtcccctg | gtgaacggcg | 1500 |
| gcatggtggc | ctcatggaca | ctgaccaggg | cccctaggga | agcctgtatg | gaggccactt | 1560 |
| cactttgaat | ggatctggga | tagaggaagg | acgcgagctg | tgggagcctg | ggtcctgggc | 1620 |
| acagcgggca | tgtcatggca | gggttcacca | gcctcctttc | agcagttccc | tagttctgcc | 1680 |
| ccagctacct | gtggttggtg | gtgggaggtt | tatttgttag | ttccttcagc | agtgactcac | 1740 |
| cacacttact | gagagcttac | cgtgtgccag | gactgccaca | ggtatgggga | tgcagtgtcc | 1800 |
| acagccccc | agaagattga | tgatagcacc | ctccatgtag | gaatggctgt | gactgcagac | 1860 |
| agggcatggg | gcggggcacc | tgtgtttgcc | acaacctcta | gagggtccct | tcatattcac | 1920 |

```
gtctgtgcgt ggggccctcc tccacccaga tctgcttccg cagcacagcc acacaagtct   1980
acagctggtg actgtggctg gcaagcaggg gaaggtgggt gggggcggca gccgtgggct   2040
ttccactggg tcccagcaga ccaagtcctg gtacaaggaa gcacgggctg gcactggcaa   2100
accctcctca gggagcagca ggccaggaac ctgggctggg actaattatt gctgaagaga   2160
gaacagggcc aagtgtccct catgtccccc cagcagccgg ggcaagcaga gaaagaaatg   2220
tcagaaccgg ggagaggccc ctgcctctgc acagggctaa acatcatgcc agctggcaag   2280
ggagaaatgg gtacagggcc caggggcatt atcacagaag aaggcaatga agggtgcgtt   2340
gggggctgag gcaacccatt ataactgcac acatcacaca ccaggatccc actaatttag   2400
actacaatgt gaatggtctt ttgaaactga gatgtgtggg ggcccagagg gagggatcca   2460
cccagctggg aggaggttag ggaggtcttc cttaaaatac ttcctgttcc gtctcagaga   2520
acccatggac actggccagg ggagggagag gaaacacatc gcaggtggag agaatcgctt   2580
gtgtgagggc acagagcggg gcaagaagac agtggtgggc tttccccagg agctgttcgg   2640
cagagggaaa gtggatgctg agctcttcct cttccctgga gcaagtccca tttcctcaga   2700
gaacacggcc cccttgggcc aaaaggacat gaagaagctc ttgctaatgc cagcctggct   2760
ctcctcatcc cgccccctgc acccctgccc ttctggctgc cctcccttct cctagctctg   2820
tccctctca cttcaggagt ctcaagtcct tcagactact ccaaagtcgg gggatctctg   2880
gatgggtagg aggtgatctc accgcctcct ctcttgcccg ggcttgtcga gatgaacttc   2940
ctgatgctgg cggcgctgaa gctgacacta gcggggcac ctccctgaca tgaacgcccc   3000
tcgagactgg gccagtgctc ctgatgcctg ggcacctgcg gaaaggcacc cagcgtggcc   3060
gccgtggcat gccttgagtg tgtgggtggg gactgttgca aactgacatt ccagctgtcc   3120
cagtccattt tgtgctgctc tcacacaacc ccggagagtg ggcgattcac aaaggacaga   3180
aatgtatctt cccacagctc tggagccagg tgccagcagg ttctgtgcct ggtgatggct   3240
ccagtctctg ctttcatgat ggtgccttgc tgctgcgtcc tccagaaggg acaaaggctg   3300
ccgtcctcac atggctgaag gtggaagggc aacgagtgaa tgtactccct ccacacagca   3360
cctacatcag gacacctgat tccattcatg gcctaatccc ctcttaaggc cccacctctt   3420
aatgctagca cattggcaac acctggattt tgcgggggaa acacgttcaa accataacac   3480
catctaaggc tgcttctgcc tgagacaagt gtgctcatgt ctgcctcaga gacggggcca   3540
aaagcagctt gctctgccct gccctggaag caggacagag gatagctgtc atctctccct   3600
tccaatgcca gctcattgtc tcaaacaaaa cttggcccct tgtgccctct aaggagtggg   3660
ttcctgtgca ggggctccaa ggttctttgt gataatagac cagggagggc aagttggttc   3720
cctctcatgc ttggcatcca ggtgtttgag ggtagctgcc cagggccctg tgttgagggc   3780
actatggtca gagctggagc aaggggggc tgggtgcatg atgagtttgc atggcagctg   3840
gaagtgtccc ctctgagtgg ctccctggat atcccggac cactggccgt gtgcaacctg   3900
agtcccggca tgaactccgc tgggaccctc cttcgtgtta acgcttcact tttcaaacag   3960
gaaatagaag gaaaacaaag ctgctttcta acaaacactt tgattttaaa gccagagtat   4020
gagtcagaaa catcatccat tgcagccagc tttacatggg aatagcccag ttcttcaaaa   4080
gaagcagctg tcatttcatg gcaccgaggc atcgtgtttc cagaagagcc acagtccctc   4140
ttgcattaag atgggttgtg acggacctct tagagaatcc gacagtttcg ggttggaaag   4200
gggatccctt ttgttctgtc tggacagtaa ggcagtgcat catctacagg tgcatccgct   4260
gcatggctgc tggcttgtgg cctgacaaaa tgcccagcat tgaaccagat gcataggtgt   4320
```

```
gaactctgga gaatcctgtt ttcagtggct ggaagacgga ggtgtaggca ccagctcaaa    4380
ctcttcacct cacgccttct atcctgcaga ccccagcagg ccacatggtg accttctatg    4440
tccatctggg acagcagtca gctgcccctg cctctgcggg gagtgagcaa tgggccgcag    4500
gatcacttgt cctgggcagc tcttctgggg gtggctttgc attgctgctg ggatttggga    4560
gtccagggcc tgtggtctcc tgggggctgc gtgcagagtg tcttccccag aaccagatgg    4620
ggaagggagc cgcagggaaa gaacgtgacc tttgggctca atcctggtat gaagccgtg     4680 ttcgttcttt tacattttcg taacgtgcag cattgggtaa atgccttctg agtttggtta    4740
gtgcttgtta aattgggcga gaacttcata aggttgcagg aagtattccg agaaatggta    4800
catgcacagt acttagcgtg gtcaccgcac atggccagca tgtaccaaac tggtccgaat    4860
tgactagaat ggggagggtg ggaagcgaca atctctacgt tctctttaac ctgaggtgtc    4920
tgatgctact tgctgggctt ctggcctgtg atgagtgctc ccactccctg ctgccctgag    4980
acctgtgtgg ctttcagggt attcttttt tctcagtgcct ttgtgtggag agccgctgtc    5040
tccctccatt ctgtgggtga tgcaggtggc gctgctgtga gctgcccctg gaggtcatgg    5100
ataggctgtc aaggacgggg cctgccattc cagagctccc gccgcctgg ggaagcgatg     5160 tgggcagtag ctcagaatgc agcttctccc tagaccctgg gccaccgggg acttgcgaga    5220
gaaagaacag ggacggggaa gactggatgg tcctgaaagc tgagaggggc cacagaagcc    5280
cagatgacac aggactatgg gagacaagtg agggcaccag cttccctggg ttgagggacc    5340 gtgatacccca ggagggcaga gagggagaca gggcccggct ggcaacctct gagcaggtga   5400
gtgggagaga gagcaggaca gagaaggcag ctctgtgttc tgctctgatc cgtctgactc    5460 cacacgatg tggagttctc tgagactcct ttccctgaat ctgagagctt actaacagaa     5520
ggccgggcct ctgagataga gatcaggcat gtaatgaatg aatgtgaatc atgaatacag    5580
ctggagcacc cctcatcagg gtagcccaca ccttacaacc gtggacacag aggccttgtt    5640
gcttccccga aagtctagtt aatgcctagt taatatctaa ttaatgacca gttaacgaca    5700
acgctcctaa ctccatcatc ccaccccctt tccccaaatt cagcacaaat ggcttcagtt    5760
tgagtttccc aaagcatctc ctcaggtgtg tggttacagc ccagccctag ggtctctggg    5820
tgcatcggct tccccctccc agatccaagt acaactgaaa ccctaacagt agaaatcatc    5880
attgctggcc cagcgctgcc accactgctt ctgttcatag cctgttttgt ttgttttag    5940 tcccttaggg actggcccta acaacaaatg aggagaagcc aagttctctg ctttctgcag    6000
acagggcctc ccctggatgg gatcttcctc tgaggcgagc ttcagatctg ctcaagcttc    6060
ctgcagtggg gccaggaggc agggcctggg caggggagac cagaacctct cggtgatgcc    6120
tccgaatggc agggctcaga cacacacacc tggctgggta agtccctgca gtgaaaaccg    6180
agacggtctt ttgcctgcca cagccccggg cagactctgc tctcaccgtg gtgccgacat    6240
cccaagtttt cagactcacc aggacccagt gacagcatct gggtcctcag agctgcatgc    6300
ggactgtccc cagttcagag cattggacag agctgggaac tgacagccct gatcaatagt    6360
cccaagagga aggccagccc tcctcctcct cggaatcctg ggtttctagg aggcagaaag    6420 gtttctgag aaacaaggct tttgaagga aggtggtgcc tggctgcatc cagaaagtga     6480
gagctaaatg gagaggctga acaaaggacg catgtgagc gcatggggag ggaaggctgg     6540
ggtgcagggc tccggcctg ctcttctgcg tccaccccgg atcctgcttt tgtccagatg     6600
ggcctcggag caccagtcac ttactccaag aagtcgtttc ctgtgccaa taatgaagat     6660
```

```
gacgcactcg gaagcttgtg ggctctgagg aggggtaag gatgcagggg ccatgcattc      6720
atcccagcac aggcagcgca tggctccgga agcagacaca ggccaggcct gggccaggag      6780
tctgccagga gccaggagcg cctacacctc cctggaggcc cacacttctc tccccagaag      6840
ctcacacgca gcgtctgagg tgcagggccc aggtgtgctg gggtgacaaa gccccgagct      6900
gtggtgatgg gagggaggaa gcgccggttt atgtctgttc tttgggctga tttgctgtct      6960
ctgtctttgt ctctaatgtc ctttgcacca ctgaccttga ggagccttt gttcctcctg       7020 tcccagtttg gtttccatgg gaacctgagt ggcagcgtca tcactttgct gaggtgaaat      7080
gcccctggat gccatgaata cctaggggaa aacctgccag agaagaataa accatccaag      7140
agacggcgct gcagggcctc acagtctgct tccatttcct ctcaggtttc agatcccta       7200 gttttgggtg cccaagttca cggagggtgc cggggaatag aagctctgtc agtccgtct       7260 ggatcttggt cctcagcaac tgtctggatc ctgacaggtg tgtgataatt acttagtgaa      7320
ttcatgggtg tgggccgtga tagaattaag tgatttgatg tcctctcgat aaatccaggt      7380
aacgacatag ggttttttga gtttgaccct ctcctgaaat ttgccatctg acaaaatgac      7440
atcatggcag agttgtaaac tgctgtggat gtatttatt taatttctca aattaaaata       7500
aaaggtaacg gtacacttaa gagtggtcac tacagccaag ctaattgaca cccactgaac      7560
tttctggaat gggccatagg atgctggaca ataggacaga tttggaatga gcagtcttcc      7620
attccaactt tagtttctgc aaagctgttg agagcatgga gccaggctgc ggggtctggg      7680
ttcaaatcct gactctacca cttaggagct gtgtgtacat gggcaggaca actggcctgc      7740
ctgagtctca gtgtaggtgt ctgtaaaatg gaatgataat agcttccatc tcacagattc      7800
actgtgtggg taaatgata gatatgaaat gctaagaaca gcacctgtac gtagtatgtc       7860
ctacatatct tactgttatc attagcatat tttgtttatt ccaagataca tttttttgg       7920 cccatttgat atctatgaaa tctaaagatt ttttttcctg tcttgggaga tagaataatg      7980
atgtgcctta caatggattg tgttttagat tcactgaaat tcattattgt tgtttttatc     8040
cctggtctgt aacatgatat ttggtaaata acaaggactc catacgtttt gcaaagagta      8100
aattctctcc ctccctactg aggccttggt ctaggtctct ccaggccttt ccttcctgga      8160
gccacagtgc ttagagacag gccactgggg tcagcatttg agctcagcta tgatcagaaa      8220
aaagcaccgt tgaggttgca gtgagccgag atcacgccac tgcactccag cctgggcgac      8280
agagagagac tccatctcaa aacaaaaaca aacaaacaaa cagaaagcac cgtcgagaaa      8340
tggctccagc gctgactagc ggccacctca tttccccct tgaccactgg gccagttggg       8400
tggctaggtt gcctcatttt gcatccttct gtatcccaa atctgaaata aaagctggaa       8460
aaaaattctt gtgaagtttg cattccaatc tataatatcc acttgctaaa aactaaaaac      8520
gatgcatctc cacaaaactc tgcaaggaaa agtatgctcc aagcgttgtc tcacagctat      8580
ggcacgcccg agggcactcc cagtatgcac ttccaaggac ggtttgagaa gtgcgggttt      8640
gatcatctat agcagatgct gctgatgcca accagcaagc cccgggcccc cgctgggtgt      8700
cccccagctg cagtggacag tcattcctgc tgacacgttc ctaccacaag ccccggcatt      8760
gatagcttgg ttttgttttg tgttttcag tgcagtaaga gcttgcctgg cctgtgtgca       8820
gagctgcctc atcctgaaat tctgggagtt gaaagcccca gggcaaccct taaccaatgg      8880
gggaaaagca ttggtgtgta atccccag cttccctggg tgggctgcag ctgagccata       8940
ttctacatga cacttccgag gatccccagt gggcatgacc tcaatcgccc acattggatg      9000 ccacaaacctg cactggcttt tctcccttcc ctgtgggtct ctctctgcac ttcctcccttt     9060
```

-continued

```
gtgcattcta ggttcacctt ccaaataaat gatgtgcact cagggccttg tctcagtctc      9120
tgacctcggg gaaacctaaa ctaagaaagt cgataccaga agcagccccg cagagtagcc      9180
cctaaaatga aattctgagc tgggatcgag ggatccctat agtgagtcgt attatgcggc      9240
cgcgaattct catgtttgac cgcttatcat cgataagctt taatgcggta gtttatcaca      9300
gttaa                                                                  9305
```

<210> SEQ ID NO 8
<211> LENGTH: 20
<212> TYPE: DNA
<213> ORGANISM: Homo sapiens
<400> SEQUENCE: 8

```
tctcttgccc gggcttgtcg                                                  20
```

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Sequence <400> SEQUENCE: 9

```
tctcttgccc gggcttgtcg                                                  20
```

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Sequence <400> SEQUENCE: 10

```
cgacaagccc gggcaagaga                                                  20
```

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence:Artificially
      Synthesized Sequence <400> SEQUENCE: 11

```
ctctcttgcc cgggcttgtc ggtac                                            25
```

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence:Artificially
      Synthesized Sequence <400> SEQUENCE: 12

```
cgacaagccc gggcaagaga ggtac                                            25
```

<210> SEQ ID NO 13
<211> LENGTH: 24
<212> TYPE: DNA
<213> ORGANISM: Artificial Sequence
<220> FEATURE:

```
<223> OTHER INFORMATION: Description of Artificial Sequence:Artificially
      Synthesized Primer Sequence

<400> SEQUENCE: 13
atgggatctt cctctgaggc gagc                                              24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 14
tcactgcaac ctcaacggtg cttt                                              24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 15
atgggatctt gaggcgagct cctc                                              24

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 16
tcactgcaac ctcaacggtg cttt                                              24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 17
tcagttccca gctctgtcca atgc                                              24

<210> SEQ ID NO 18
<211> LENGTH: 16
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 18
gatcccatcc agggga                                                       16

<210> SEQ ID NO 19
<211> LENGTH: 16
<212> TYPE: DNA
<213> ORGANISM: Artificial Sequence
<220> FEATURE:
<223> OTHER INFORMATION: Description of Artificial Sequence:Artificially
```

Synthesized Sequence

<400> SEQUENCE: 19
ggaggcaggt gaggag                                                          16

<210> SEQ ID NO 20
<211> LENGTH: 17
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 20
ccaagttctc tgctttc                                                         17

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 21
agctgagctc aaatgctgac                                                      20

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 22
gcagctcctg gattcaatta c                                                    21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 23
gcctatgttc ttcttcgcct c                                                    21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 24
aggactgttc gtgttcagct c                                                    21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence:Artificially
      Synthesized Primer Sequence

```
<400> SEQUENCE: 25
gtgcacctcc tgagaaaact c                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 26
ccaacaggtg tcaacatgtt g                                              21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 27
caatcttctg cttggcaagt c                                              21

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 28
ggagctgcag aggatgattg                                                20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 29
ccacaaagat ggtcaccgtc                                                20

<210> SEQ ID NO 30
<211> LENGTH: 16
<212> TYPE: DNA
<213> ORGANISM: Artificial Sequence
<220> FEATURE:
<223> OTHER INFORMATION: Description of Artificial Sequence:Artificially
      Synthesized Sequence

<400> SEQUENCE: 30
tcccctggat gggatc                                                    16

<210> SEQ ID NO 31
<211> LENGTH: 16
<212> TYPE: DNA
<213> ORGANISM: Artificial Sequence
<220> FEATURE:
<223> OTHER INFORMATION: Description of Artificial Sequence:Artificially
      Synthesized Sequence
```

```
<400> SEQUENCE: 31
gatcccatcc agggga                                                     16
```

The invention claimed is:

1. An isolated DNA of the following (a) or (b):
   (a) a DNA encoding a protein comprising the amino acid sequence of SEQ ID NOs: 2, 4, or 6, or
   (b) a DNA comprising the entire coding region of nucleotide sequence of SEQ ID NOs: 1, 3, or 5.

2. An isolated protein encoded by the DNA of claim 1.

3. An expression vector comprising the DNA of claim 1.

4. An isolated host cell transformed with the expression vector of claim 3.

5. A method for producing a protein comprising the amino acid sequence of SEQ ID NO: 2, 4, or 6, the method comprising the steps of culturing the host cell of claim 4 and recovering the protein expressed from the expression vector from said host cell or the culture supernatant thereof.

6. A method of screening for a candidate compound as an apoptosis controlling agent, the method comprising the steps of:
   (a) contacting a test sample with the protein of claim 2,
   (b) detecting the binding activity of the test sample to said protein, and
   (c) selecting a compound having the activity to bind to said protein,
thereby identifying the candidate compound as a potential apoptosis controlling agent.

7. A method of screening for a candidate compound as an apoptosis controlling agent, the method comprising the steps of:
   (a) contacting a test sample with the protein of claim 2, and bcl-2 protein,
   (b) measuring the binding activity of said protein to bcl-2 protein, and
   (c) selecting a compound capable of decreasing or increasing the binding activity measured in the step (b) compared to that measured in the absence of the test sample,
thereby identifying the candidate compound as a potential apoptosis controlling agent.

8. An apoptosis inducing agent comprising the vector of claim 3 as an effective ingredient.

* * * * *

UNITED STATES PATENT AND TRADEMARK OFFICE
CERTIFICATE OF CORRECTION

PATENT NO. : 7,569,351 B2  Page 1 of 1
APPLICATION NO. : 10/343733
DATED : August 4, 2009
INVENTOR(S) : Nakamura et al.

It is certified that error appears in the above-identified patent and that said Letters Patent is hereby corrected as shown below:

Column 53, line 4, please insert:

--<210> 32
  <211> 20
  <212> DNA
  <213> Artificial Sequence

<220>
  <223> Description of Artificial Sequence: p53-binding site consensus sequence
<400> 32
rrrcwwgyyy rrrcwwgyyy--.

Signed and Sealed this

Twenty-fourth Day of November, 2009

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,569,351 B2 | Page 1 of 1 |
| APPLICATION NO. | : 10/343733 | |
| DATED | : August 4, 2009 | |
| INVENTOR(S) | : Nakamura et al. | |

It is certified that error appears in the above-identified patent and that said Letters Patent is hereby corrected as shown below:

On the Title page,

Item [*] Notice: Subject to any disclaimer, the term of this patent is extended or adjusted under 35 USC 154(b) by (25) days Delete the phrase "by 25 days" and insert -- by 129 days --

Signed and Sealed this

Twenty-sixth Day of January, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,569,351 B2 | Page 1 of 1 |
| APPLICATION NO. | : 10/343733 | |
| DATED | : August 4, 2009 | |
| INVENTOR(S) | : Nakamura et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 465 days.

Signed and Sealed this
Twenty-sixth Day of June, 2012

David J. Kappos
*Director of the United States Patent and Trademark Office*